(12) United States Patent
Richardson et al.

(10) Patent No.: US 11,857,370 B2
(45) Date of Patent: Jan. 2, 2024

(54) METHOD AND SYSTEM FOR VISUALLY ASSISTING AN OPERATOR OF AN ULTRASOUND SYSTEM

(71) Applicant: EXACT IMAGING INC., Ontario (CA)

(72) Inventors: Jeff Richardson, Ontario (CA); Jerrold Wen, Ontario (CA); Brian C. Wodlinger, Ontario (CA)

(73) Assignee: NATIONAL BANK OF CANADA, Montreal (CA)

( * ) Notice: Subject to any disclaimer, the term of this patent is extended or adjusted under 35 U.S.C. 154(b) by 481 days.

(21) Appl. No.: 16/495,923

(22) PCT Filed: Mar. 20, 2018

(86) PCT No.: PCT/CA2018/050336
§ 371 (c)(1),
(2) Date: Sep. 20, 2019

(87) PCT Pub. No.: WO2018/170592
PCT Pub. Date: Sep. 27, 2018

(65) Prior Publication Data
US 2020/0129154 A1 Apr. 30, 2020

Related U.S. Application Data

(60) Provisional application No. 62/473,874, filed on Mar. 20, 2017.

(51) Int. Cl.
*A61B 8/00* (2006.01)
*A61B 8/08* (2006.01)

(52) U.S. Cl.
CPC .............. *A61B 8/463* (2013.01); *A61B 8/085* (2013.01); *A61B 8/4245* (2013.01); *A61B 8/466* (2013.01);
(Continued)

(58) Field of Classification Search
CPC ......... A61B 8/463; A61B 8/085; A61B 8/529; A61B 8/466; A61B 8/483; A61B 8/5261; A61B 8/4245; A61B 8/5292
See application file for complete search history.

(56) References Cited

U.S. PATENT DOCUMENTS 5,787,889 A * 8/1998 Edwards .................. A61B 8/14
600/443
5,876,345 A * 3/1999 Eaton .................. G01S 15/8918
600/463

(Continued)

FOREIGN PATENT DOCUMENTS

| WO | 03039370 A1 | 5/2003 |
|---|---|---|
| WO | 2010140075 A2 | 12/2010 |
| WO | 200106924 | 2/2011 |

*Primary Examiner* — Oommen Jacob
(74) *Attorney, Agent, or Firm* — Tarolli, Sundheim, Covell & Tummino, LLP

(57) ABSTRACT

A system and method for visually assisting an operator of an ultrasound system are provided. In an aspect, the method involves receiving imaging data of an anatomical region using a first coordinate system, the imaging data marked with a landmark for identifying the anatomical region; transforming the imaging data of the anatomical region from the coordinate system to a cylindrical coordinate system; displaying a live ultrasound image of the anatomical region as received from an ultrasound transducer; receiving positional information from the ultrasound transducer corresponding to an alignment point of the anatomical region; and displaying a transformed image from the transformed imaging data of the anatomical region corresponding to the alignment point using the landmark; wherein the transformed image and the live ultrasound image are displayed simultaneously. In another aspect, the method involves generating and transforming a 3D model of the first anatomical regions.

33 Claims, 27 Drawing Sheets

(52) U.S. Cl.
CPC ............ *A61B 8/483* (2013.01); *A61B 8/5261* (2013.01); *A61B 8/5292* (2013.01)

(56) References Cited

U.S. PATENT DOCUMENTS

| | | | |
|---|---|---|---|
| 7,066,889 B2 * | 6/2006 | Taylor | A61B 8/12 600/459 |
| 9,437,043 B2 * | 9/2016 | Schauf | A61B 8/4488 |
| 2008/0221425 A1 | 9/2008 | Olson et al. | |
| 2011/0046483 A1 | 2/2011 | Fuchs et al. | |
| 2011/0178389 A1 * | 7/2011 | Kumar | G06T 7/33 600/411 |
| 2012/0150035 A1 * | 6/2012 | Seip | A61B 8/12 600/439 |
| 2013/0131501 A1 * | 5/2013 | Blaivas | A61B 8/4455 600/424 |
| 2014/0073907 A1 * | 3/2014 | Kumar | A61B 10/0241 600/414 |
| 2017/0181795 A1 * | 6/2017 | Debruyne | A61B 18/1492 |
| 2017/0258446 A1 * | 9/2017 | Mao | A61B 8/4254 |
| 2018/0153505 A1 * | 6/2018 | Cadieu | A61B 8/4254 |
| 2020/0383658 A1 * | 12/2020 | Wang | A61B 8/467 |

* cited by examiner

To Anus

METHOD AND SYSTEM FOR VISUALLY ASSISTING AN OPERATOR OF AN ULTRASOUND SYSTEM

CROSS-REFERENCE TO RELATED APPLICATIONS

This application is the National Stage of International Patent Application No. PCT/CA2018/050336, filed Mar. 20, 2018, which claims the benefit of U.S. Provisional Patent Application No. 62/473,874, filed Mar. 20, 2017, the disclosure of which is incorporated herein by reference in its entirety.

BACKGROUND

Magnetic Resonance Imaging (MRI) and ultrasound fusion has become an important technique for targeted biopsy of prostate cancer because there are some cancers that MRI is more sensitive to detecting than ultrasound. It is known that MRI can detect prostate cancer. However, it is impractical to perform the biopsy inside the MRI magnet due to safety restrictions, material restrictions, lack of real time feedback, and the high cost of MRI time. Instead, the target, such as a prostate and/or lesion in or on the prostate, is located through imaging with MRI and then the image or sequence of images is "fused" with live ultrasound for assisting a urologist in the taking of the prostate biopsy. Several techniques have been proposed to accomplish this fusion, generally involving both a tracking component and a software/workflow component. Existing tracking components include electromagnetic sensors and mechanical tracking arms, while known software workflows include rigid and elastic registration of the MM and the ultrasound images of the prostate using semi-automated boundary segmentation.

Also, a radiologist may review the MRI and then generate a report on suspicious regions in the prostate for the urologist. The urologist then may view the report to assist in locating the prostate and/or lesion, while using ultrasound to assist in the manual taking of the targeted biopsy of the prostate.

SUMMARY

The MRI data of the prostate provides 3-dimensional (3D) information about the location of the prostate and/or lesions on or in the prostate. Ultrasound imaging provides a 2-dimensional (2D) image. The urologist may be performing a cognitive fusion in their head to process the 3D location of the prostate and/or lesion, while viewing the 2D ultrasound image during the taking of the targeted biopsy of the prostate.

In an aspect, there are provided methods and systems that may assist in reducing the mental load on the urologist by improving accuracy and simplicity of the presented processed MRI and ultrasound images by transforming the 3D MRI data to 2D data compatible for viewing with live ultrasound image data. Therefore, by reducing the mental load on the urologist, this may lead to a decrease in errors (e.g. left/right swap) during the taking of targeted biopsies of the prostate.

Also, a radiologist may review the MRI data of the prostate and generate a report on suspicious areas of the imaged prostate. The suspicious area or areas are identified in the report as a region or regions in a multiple region model (e.g. 39 regions) of the prostate.

In another aspect, there are provided methods and systems for providing a 3D model of a prostate with multiple regions, converting the 3D model to 2D data compatible for viewing with live ultrasound image data, and showing by a 2D graphical representation of the model prostate the region or regions of the prostate being imaged by the live ultrasound probe.

In an embodiment, images from a MRI scan and an ultrasound scan are displayed synchronously on the screen so that the urologist can identify and target the lesions. In another embodiment a representation of a prostate and images of an ultrasound scan are displayed synchronously on the screen so that the urologist can identify and target the lesions.

An embodiment system includes a side fire ultrasound transducer (e.g. an EV29L side-fire transducer). The disclosed apparatus and system also includes an Inertial Monitoring Unit (IMU) that tracks the Roll, Pitch and Yaw angle of the side-fire ultrasound transducer. A processing unit of the system is configured to process MRI image and/or report data so that it corresponds to ultrasound image data obtained by the side-fire ultrasound transducer. When performing the processing it is noted that (in contrast to existing solutions) the present disclosure's position of the probe, orientation of the ultrasound element array on the probe, and additional information including alignment points are used to perform the fusion, which may reduce the number and complexity of the registration points. In an embodiment, this registration can be accomplished using a single line annotated onto the midline slice of the MRI, and a single button click on the ultrasound to identify the same midline view thereby avoiding time consuming and error-prone boundary segmentation of the edges of the prostate. In another embodiment, only the roll angle of the ultrasound-transducer is used.

BRIEF DESCRIPTION OF THE FIGURES

Note that in FIGS. 1A-3F a 3D coordinate legend corresponding to the 3D orientation of the figure is provided in the top left corner of the page for readability.

FIG. 6A (SHEET 16/27) is an embodiment partial user interface (UI) for the workflow of FIG. 5

FIG. 6B (SHEET 16/27) is an alternate embodiment partial UI for the workflow of FIG. 5.

LISTING OF REFERENCE NUMERALS USED IN THE DRAWINGS

Figure 1A:
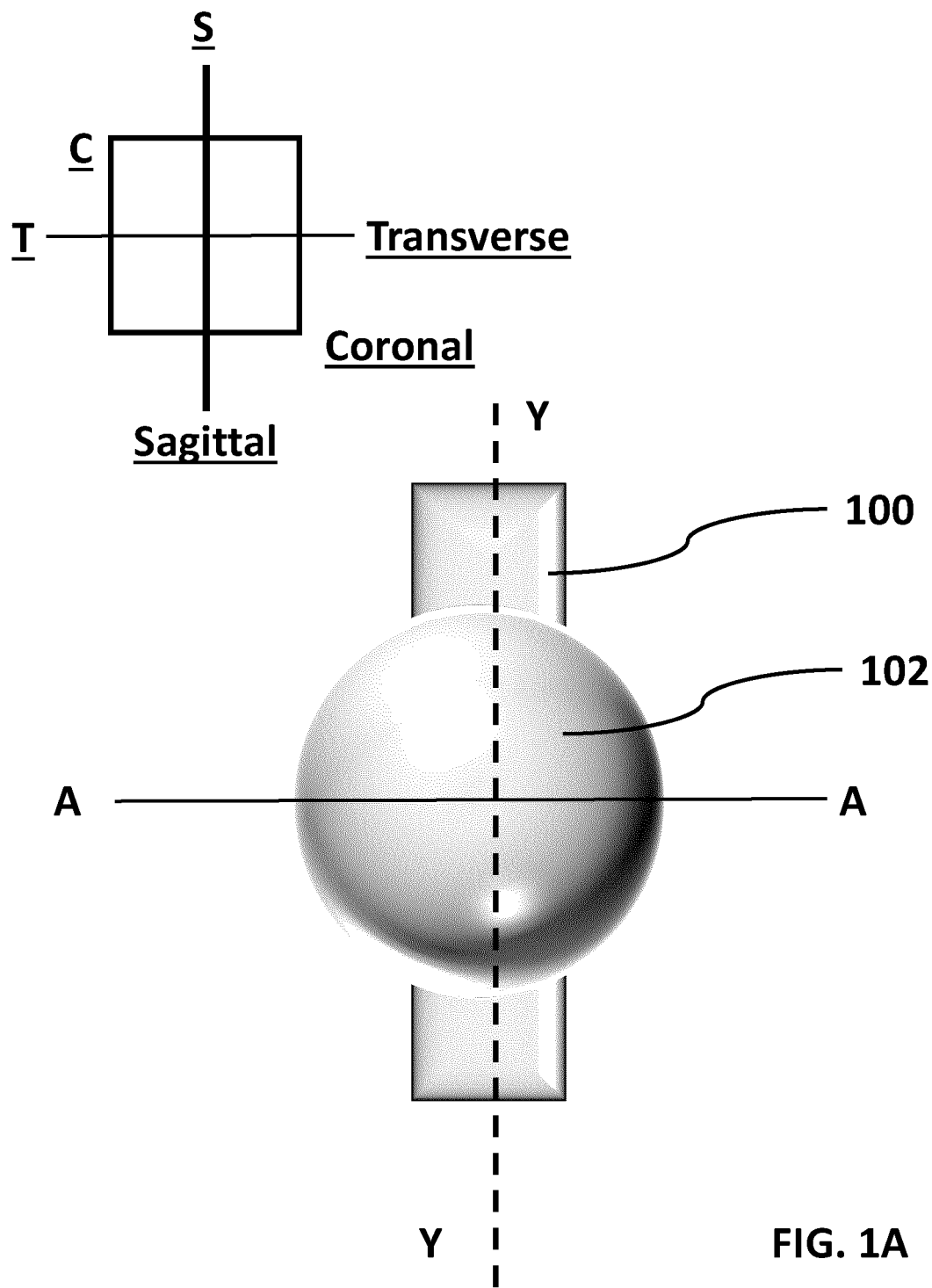
FIG. 1A (SHEET 1/27) is a coronal plane representative view of a prostate and rectum.

100—Rectum
102—Prostate
200—Transducer Probe
300—Lesion
400—Left Calibration Button
402—Middle Calibration Button
404—Right Calibration Button
500—MRI Calibration Button
600—Display Device+Input Device
602—Processing Unit
604—Input Device
606—Trans-rectal Side Fire Ultrasound Transducer Probe
608—Data Store
700—Grid
702—Line
704—Point
800—Landmark
802—Identified Lesion

DETAILED DESCRIPTION OF THE NON-LIMITING EMBODIMENTS

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the invention is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the invention is limited to the subject matter provided by the claims, and that the invention is not limited to the particular aspects depicted and described.

Referring now to FIG. 1A, FIG. 1A (SHEET 1/27) is a coronal plane representative view of a prostate and rectum. Typically, MRI devices image cross sectional "slices" of the human body on one or more planes. FIG. 1 depicts how an existing MRI device might take a single cross sectional image (i.e., transverse cross sectional image as indicated by the axis labelled A-A) of a prostate 102 and a rectum 100. In this example the image is taken along the axis labelled. A-A that is at or near the mid-line of the prostate 102. Note that in FIG. 1A the axis labelled A-A represents the transverse plane. It will be appreciated that an MRI device may take one or more transverse cross sectional images at different points along the dotted axis Y-Y (i.e., towards the head or towards the feet). These transverse cross-sectional images, when sequenced and combined, would then provide cross-sectional image of the entire prostate 102 along the transverse plane.

Figure 1B:
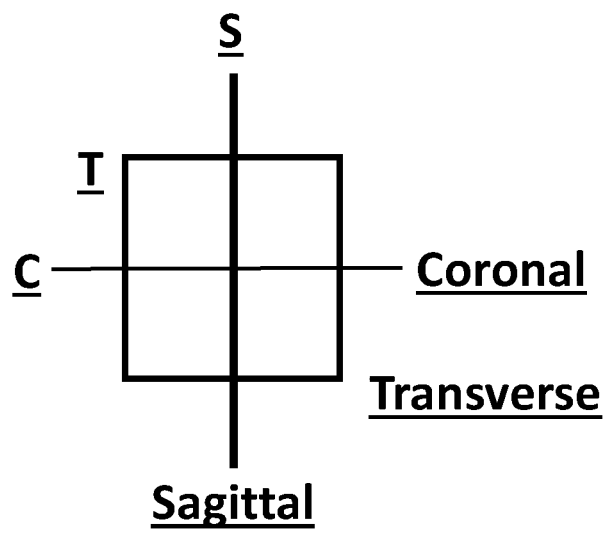
FIG. 1B (SHEET 2/27) is a transverse plane representative view of FIG. 1A along the transverse plane marked A-A in FIG. 1A and A-A in FIG. 1B.
Figure 1B:
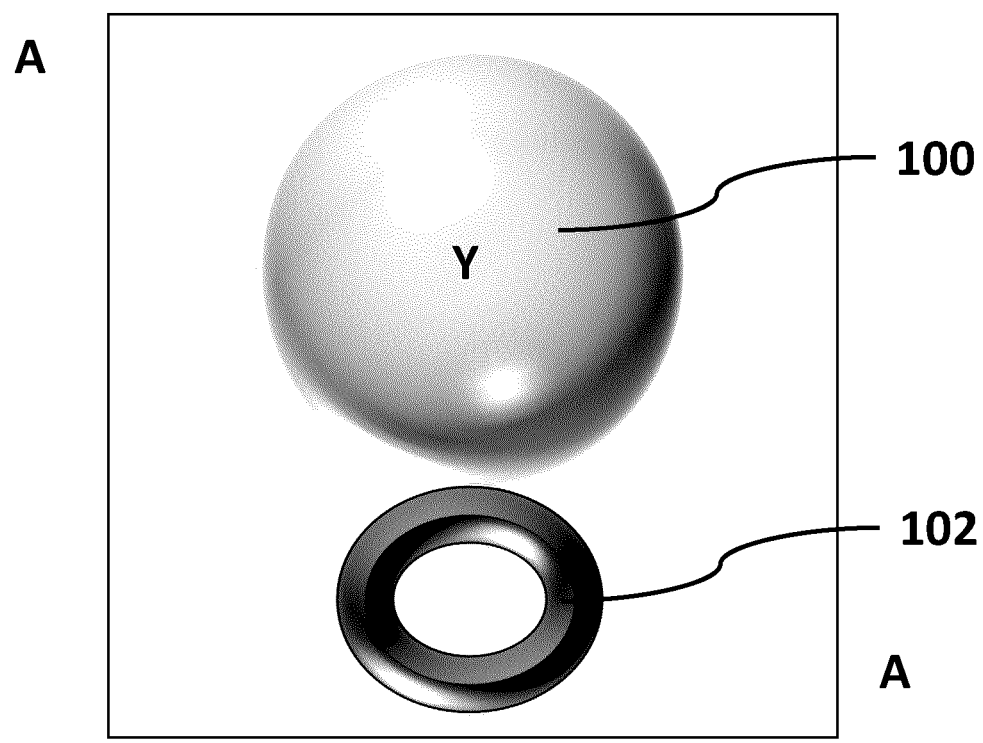

FIG. 1B (SHEET 2/27) is a transverse plane cross sectional representative view of FIG. 1A along the transverse axis marked A-A in FIG. 1A (i.e., the transverse plane marked A-A in FIG. 1B). In this figure a single transverse cross sectional representation of a prostate 102 and rectum 100 is depicted. It will be appreciated that imaging the entire prostate 102 will require a sequence of these cross-sectional images, with each of these cross-sectional images taken along the dotted axis marked Y-Y in FIG. 1A and shown as Y in this figure.

Figure 2A:
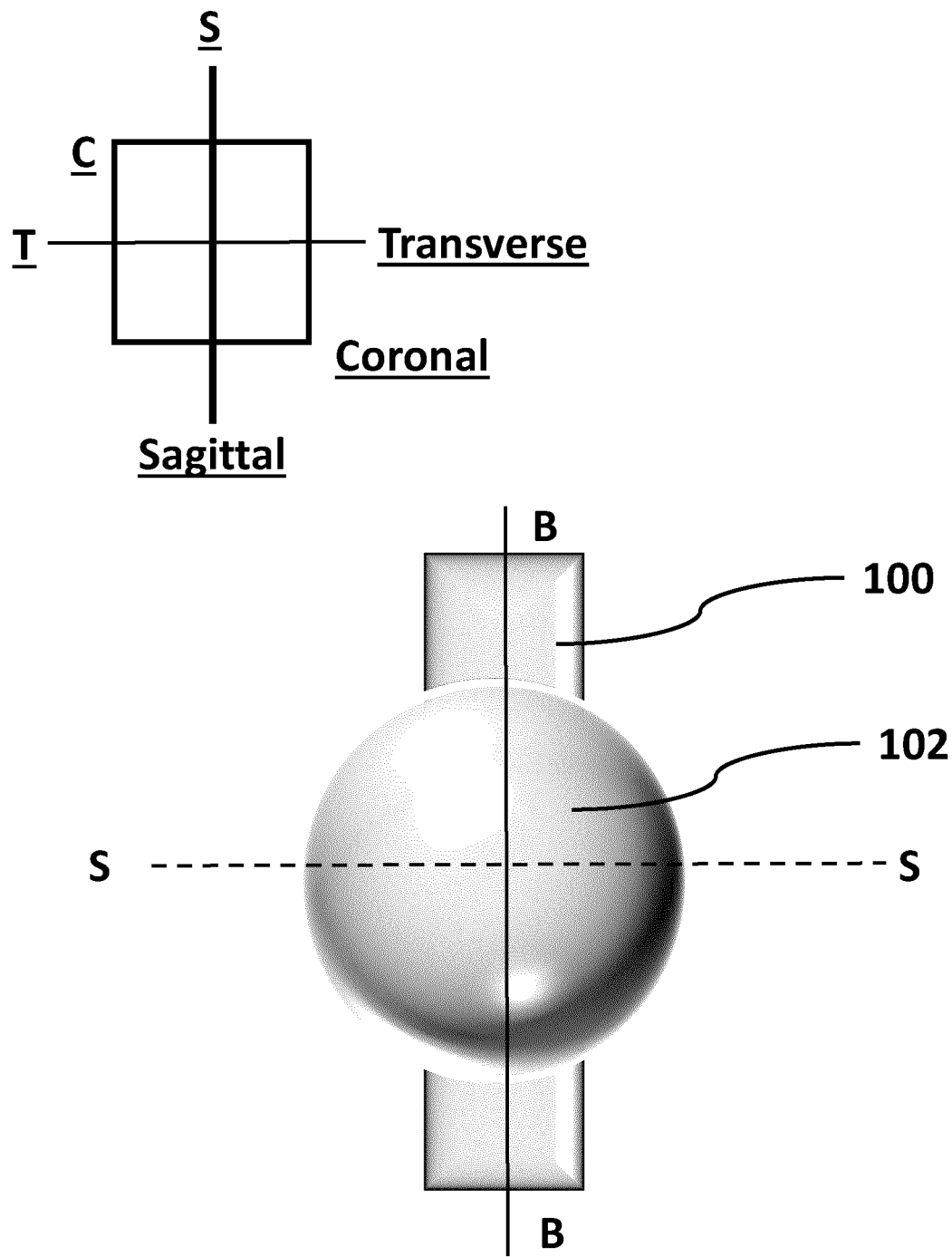
FIG. 2A (SHEET 3/27) is a coronal plane representative view of a prostate and rectum.

FIG. 2A (SHEET 3/27) is a coronal plane representative view of a prostate 102 and rectum 100. FIG. 2A depicts how an existing MRI device might take a single sagittal cross sectional image (i.e., an image along the sagittal plane as shown by the axis labelled B-B) of a prostate 102 and a rectum 100 at a point along the dotted axis labelled S-S. In this example the image is taken along the axis labelled B-B which is at or near the sagittal mid-line of the prostate 102. It will be appreciated that an MRI device may take one or more sagittal cross sectional images at different points along the dotted axis S-S (i.e., towards the left and/or the right). These sagittal cross-sectional images, when sequenced, would then provide a cross-sectional image of the entire prostate along the sagittal plane.

Figure 2B:
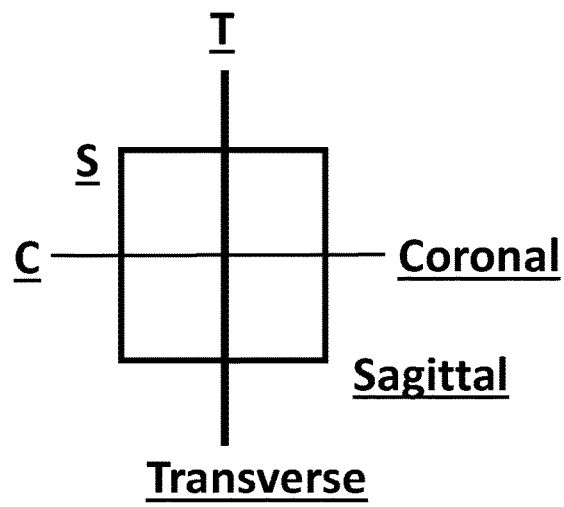
FIG. 2B (SHEET 4/27) is a sagittal plane representative view of FIG. 2A along the sagittal plane marked. B-B in FIGS. 2A and 2B.
Figure 2B:
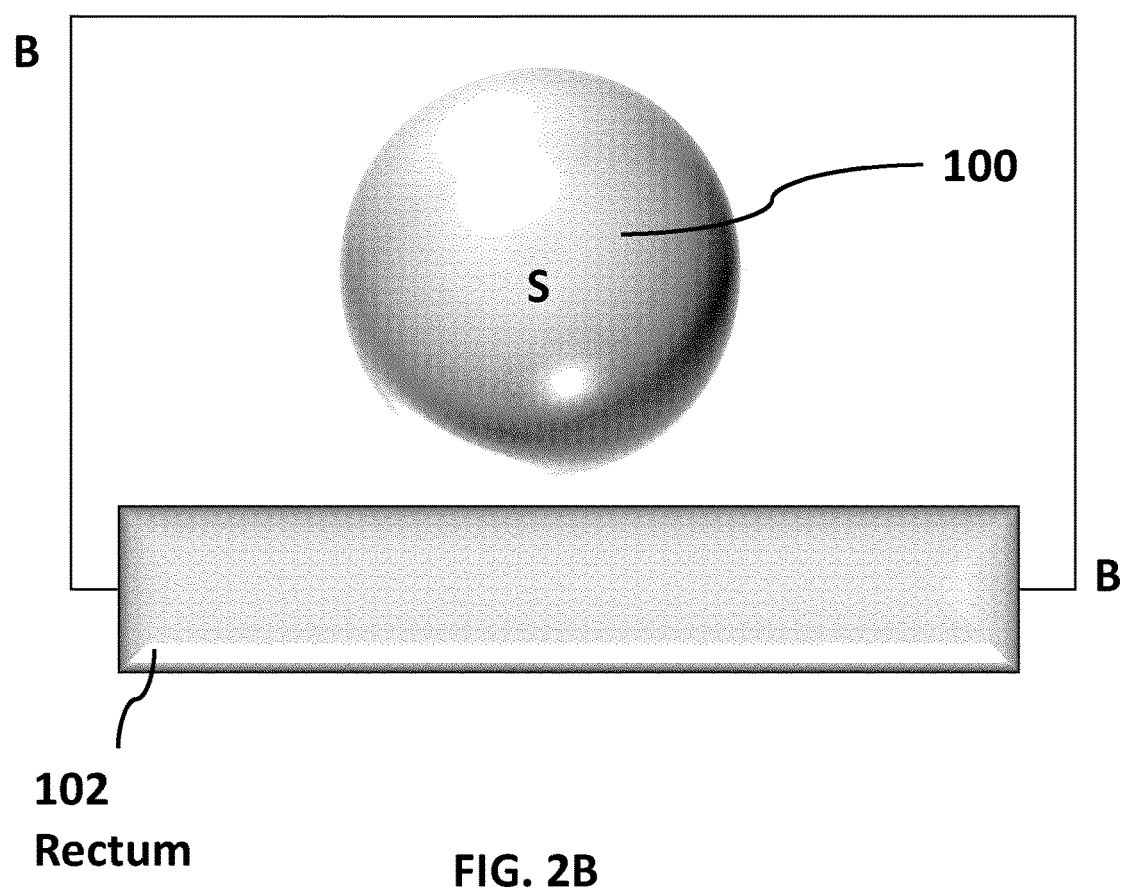

FIG. 2B (SHEET 4/27) is a sagittal plane cross sectional representative view of FIG. 2A along the sagittal plane marked by the axis B-B in FIG. 2A and the plane B-B in FIG. 28. This figure illustrates the orientation of an image taken along the sagittal plane (as shown by the axis labelled B-B in FIG. 2A) compared to an cross-sectional image taken along the transverse plane as depicted in FIG. 1B. It will be appreciated that imaging the entire prostate 102 will require a sequence of these cross-sectional images, with each of these cross-sectional images taken along the dotted axis marked S-S in FIG. 2A (and shown as S in FIG. 28).

Figure 2C:
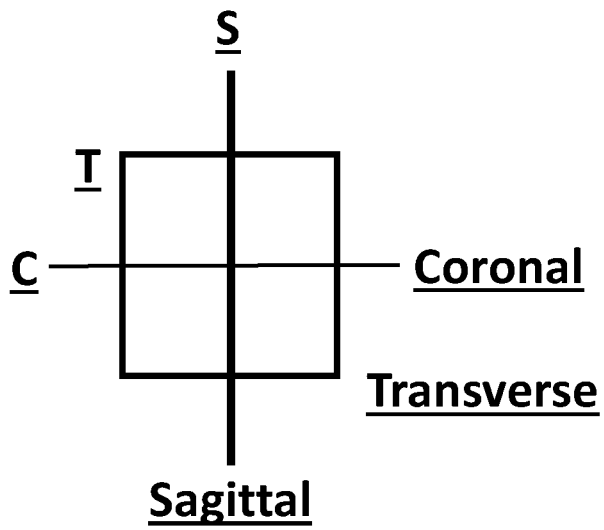
FIG. 2C (SHEET 5/27) is a transverse plane view of the prostate and rectum of FIG. 2A. The line B-B represents the sagittal plane.
Figure 2C:
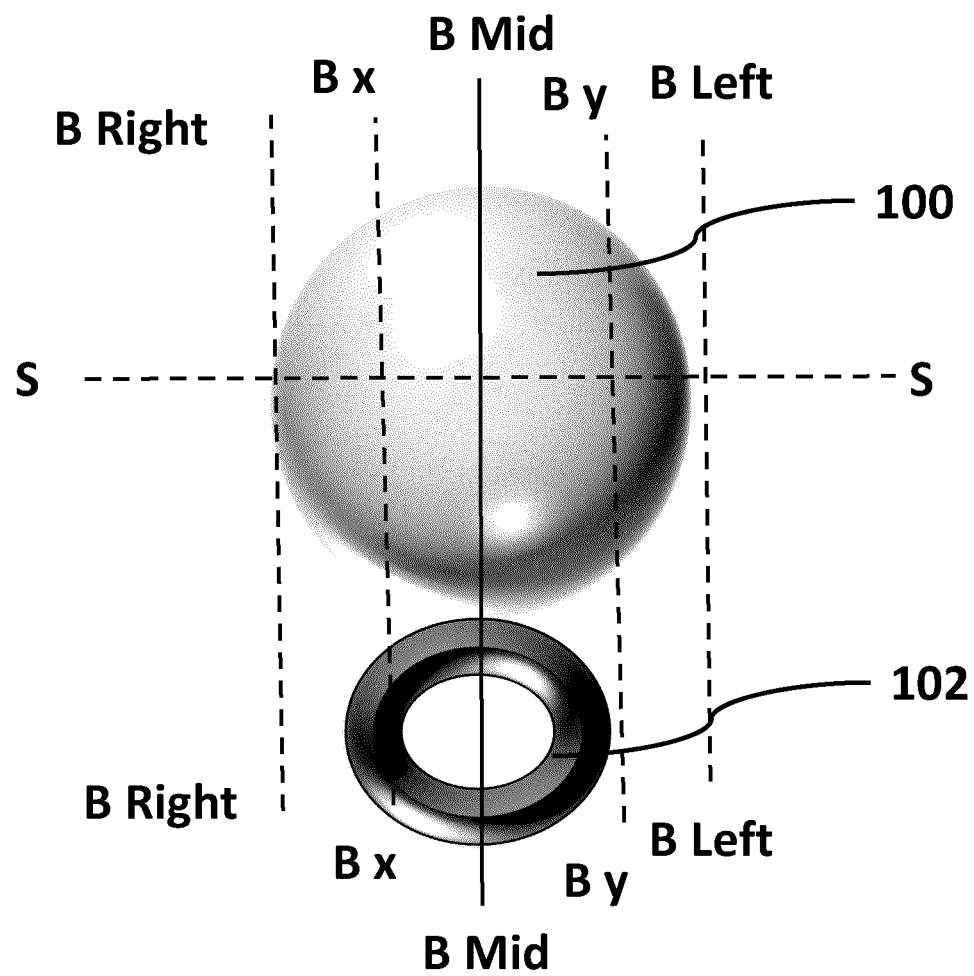

FIG. 2C (SHEET 5/27) is a transverse plane view of the prostate and rectum of FIG. 2A. The axes marked as BRight, BLeft, BMid, Bx, and By represent cross-sections along the sagittal plane. This figure depicts how an existing MRI device might take a sagittal cross sectional image of a prostate and a rectum along the axis marked B Mid-B Mid in this figure (i.e., the same axis marked B-B in FIG. 2A and the plane marked B-B in FIG. 2B).

Figure 2D:
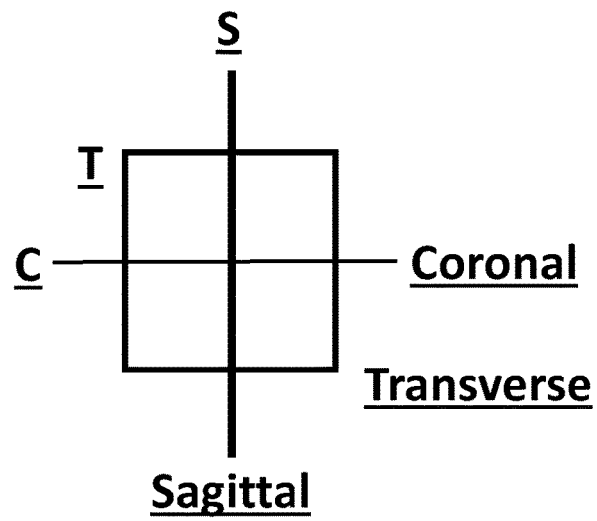
FIG. 2D (SHEET 6/27) is a second transverse plane view of the prostate and rectum of FIG. 2A. The line B-B represents the sagittal plane.
Figure 2D:
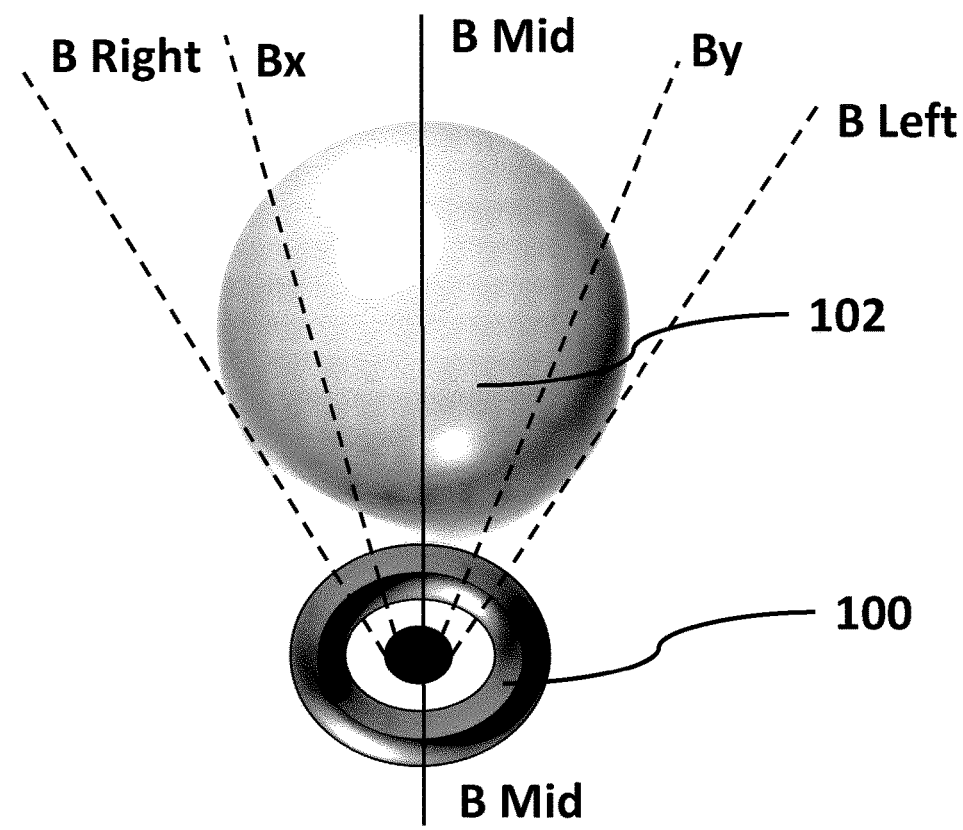

FIG. 2D (SHEET 6/27) is a second transverse plane view of the prostate and rectum of FIG. 2A. A trans-rectal side-fire transducer probe 200 is also depicted to illustrate how a trans-rectal side-fire ultrasound transducer probe 200 might image the prostate 102.

As is depicted in FIG. 1A-FIG. 2C, existing MRI imaging devices are typically configured to take transverse, coronal, or sagittal cross sectional images that are perpendicular relative to the other two planes. For example, a sagittal MRI cross-sectional image would be perpendicular to both the transverse and coronal planes. When scanning the entirety of a prostate 102, then, a series of sagittal MRI cross-sectional images, (each be perpendicular to both the transverse and coronal planes) would be used to build a representation of the entire prostate 102. That is, a sagittal cross-sectional representation of the entire prostate 102 can be constructed by effectively "stacking" (or "sandwiching") the individual sagittal cross-sectional images.

A side-fire ultrasound imaging device (as might be used in the rectum), in contrast and as depicted in FIG. 2D, is configured to capture cross-sectional images along a path defined by an arc (when in a transverse plane view). That is, the cross-sectional images captured by an ultrasound imaging device would generally be at oblique angles relative to the coronal and/or sagittal planes. When viewed in a transverse plane view, the cross-sectional images would appear to be "fan-like". The skilled person would understand that the "fan-like" images are in a cylindrical coordinate system.

It will be understood that, depending on the position of the ultrasound imaging device in the rectum, a cross-section image that is parallel to the coronal plane or the sagittal plane may also be captured. For example, an ultrasound image captured at the axis marked B-B in FIG. 2A (and BMid-BMid in FIG. 2D) would result in an ultrasound cross-sectional image that would be parallel to the sagittal plane. Other ultrasound images captured in this series, however, would be at oblique angles relative to the coronal and/or sagittal plane (e.g., an image at the axes marked Bx-Bx, By-By, etc).

For instance, one or more ultrasound scans of the prostate 102 and part of the rectum can be taken as the transducer probe 200 is rolled in the rectum. In this example, the ultrasound scans may be taken at the axes marked by (and points in between) B-Left, B-x, B-Mid, B-y, and B-Right. It should be noted that in this example the plane marked by B-Mid would correspond to a sagittal MRI image of a prostate taken at the same sagittal plane (i.e., B-Mid).

In some embodiments the transducer probe 200 may be configured to provide a continuous data feed to the processing unit so that the plane being viewed will be updated in real time or near real time as the transducer probe 200 is rolled in the rectum.

It will be appreciated that in the example depicted in FIG. 2D an ultrasound cross-sectional image that is parallel with the transverse plane would be difficult, if not impossible to capture. This is because it would be physically difficult to position the side-fire ultrasound transducer probe 200 in the rectum in a way that would allow for an image to be captured parallel to the transverse plane.

In the examples depicted in FIG. 2C and FIG. 2D, the MRI image of the patient's prostate at the axis marked B-Mid corresponds to the ultrasound image of the patient's prostate at the axis B-Mid. These two images can be used as a basis for fusing the sequence of MRI images that capture the entire prostate (as would be captured as shown by FIG. 2C B-Right to B-Left) with the sequence of ultrasound images that capture the entire prostate (as would be captured as shown by FIG. 2D B-Right to B-Left).

In this example, a processing unit 602 may be configured to resample the sequence of the MRI images of the patient's prostate (that capture the entire prostate) so that they correspond to the sequence of ultrasound images of the patient's prostate (that capture the entire prostate as depicted in FIG. 2D). For instance, in an embodiment the MRI image B-Right may, by way of a resampling, be "mapped"(or registered) to the Ultrasound image B-Right so that the combined view would provide an MRI and ultrasound image at the plane marked by the axis B-Right. The other MRI images (e.g., Bx, By, B-Left) would be likewise mapped (or registered), via a resampling, to the ultrasound images corresponding to Bx, By, and B-Left. Note that in this embodiment, no resampling is required for the MM image at the plane marked by the axis B-Mid since the ultrasound image would be on the same plane (i.e., B-Mid).

In another embodiment MRI images of the patient's prostate may be resampled and fused with the ultrasound image of the patient's prostate "on-the-fly" once the dimensions of the prostate are known. This is useful in embodiments where the ultrasound imaging device is configured to provide a stream of image data (such as a "video" stream). In an example, a user of an ultrasound imaging device would, while performing an initial ultrasound scan of the prostate, identify the rightmost edge, the leftmost edge, and the midline of the prostate. Once this information has been entered into the ultrasound imaging device the MRI image data corresponding to the prostate is resampled so that it maps to a corresponding ultrasound image on the display device of the ultrasound imaging device.

In some embodiments it may be necessary to interpolate some of the MRI imaging data so that it will match a corresponding ultrasound image at a particular angle. This may be necessary when the gaps between sequential sagittal MRI images is greater than a set amount. For example, in the case where the MRI imaging data is very tightly sampled (e.g., 0.1 mm), interpolation of the MRI imaging data may not be required. In other example where the MRI imaging data is not as tightly sampled (e.g., around 1.5 mm), interpolation of the MRI imaging data may be necessary so that the MRI imaging data will match the corresponding ultrasound image at a particular angle.

Figure 2E:
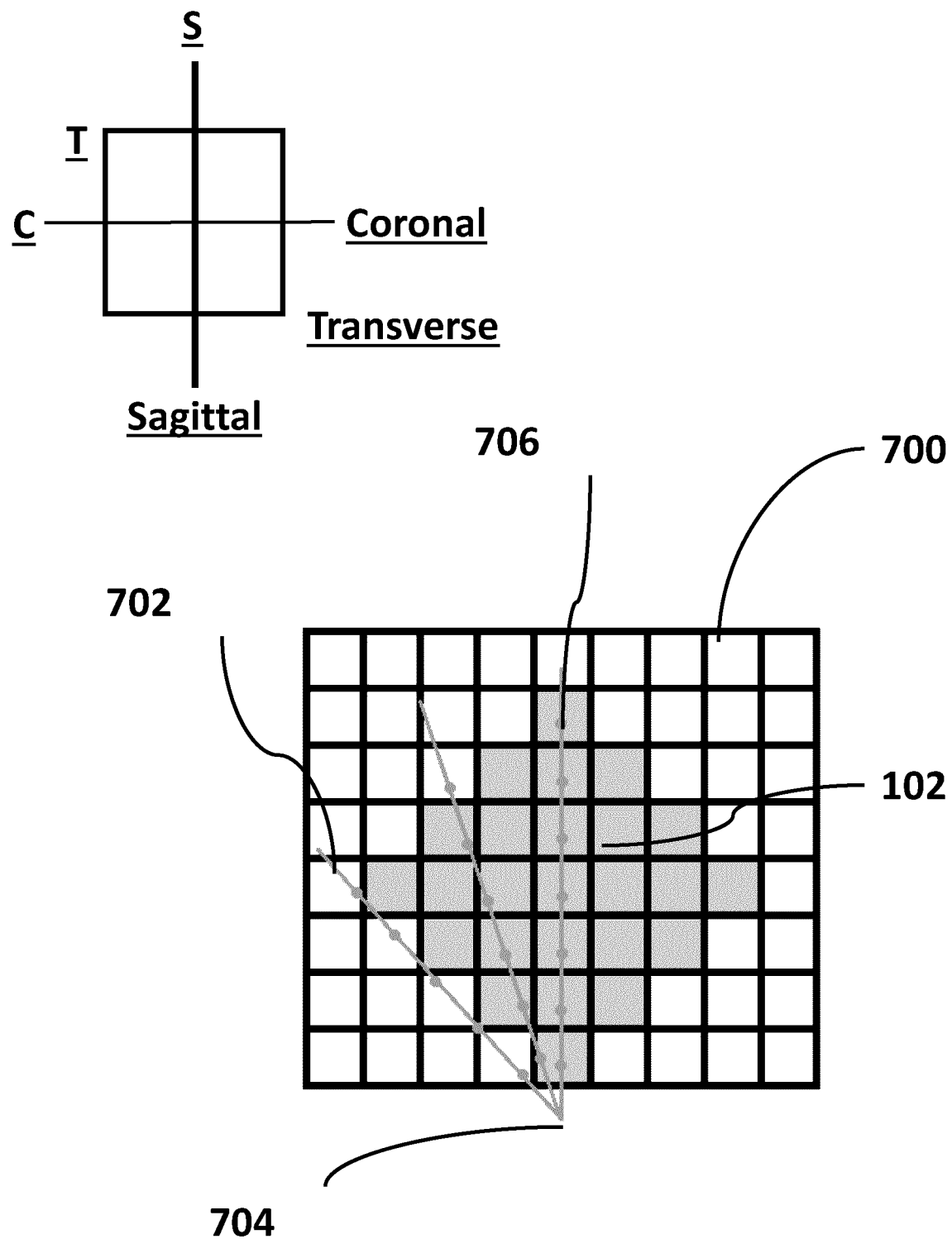
FIG. 2E (SHEET 7/27) is a representation of a transverse plane view of the prostate and rectum of FIG. 2A.

An example of how MRI images may be mapped (or registered) to a corresponding ultrasound "fan" image is provided in FIG. 2E (SHEET 7/27). In this example the "grid" 700 represents an MRI transverse slice similar to the one shown in FIG. 1A and FIG. 1B. The shaded boxes in the grid 700 represent the prostate 102 as it might appear in a digital MRI image. The lines 702 radiating from a point 704 represent "fan" slices and the dots 706 represent the sample points for determining the pixel values of the MRI transverse slice. During the resampling process, one or more resampling algorithms can be used. These include, but are not limited to, nearest neighbor, bi-linear interpolation, and/or bi-cubic. After resampling, pixels from the original sampled pixels of the transverse MRI slice will be "mapped" (or registered) to one or more "fan" slices. In some examples, a sampled pixel of a transverse MRI slice may be mapped (or registered) to many corresponding "fan" slices.

Once the MRI data has been merged with the ultrasound imaging data, the data from both images can be displayed on the ultrasound display device simultaneously. For instance, in some embodiments the MRI image corresponding to the ultrasound image can be displayed side-by-side on the ultrasound imaging device. This would allow a user of the device to compare the MRI image to the corresponding ultrasound image. This will provide a more complete view of the area of the prostate being examined, including any lesions. This enhanced prostate images would allow surgeons and/or urologists to perform procedures on the prostate 102 (such as biopsies of lesions, etc.) while live-imaging the prostate. This would not be possible in an MRI device, and the ultrasound image alone would not provide sufficient information for the surgeon/urologist to perform the procedure. In an embodiment, the lesion is modelled as a sphere.

Figure 3A:
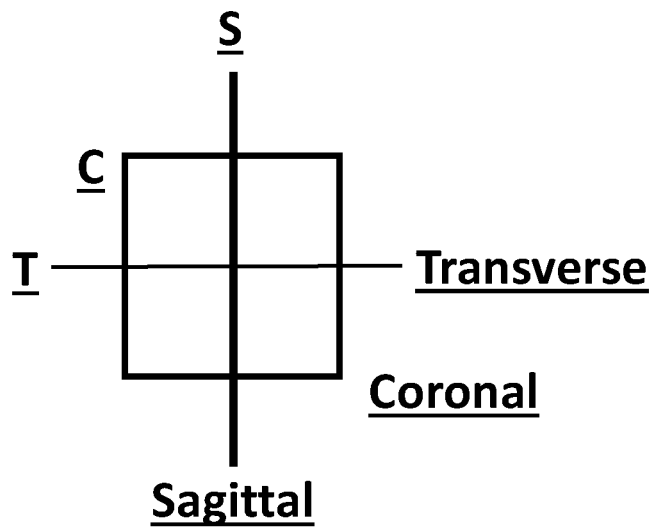
FIG. 3A (SHEET 8/27) is a coronal plane representative view of a prostate and rectum, the prostate having a lesion.
Figure 3A:
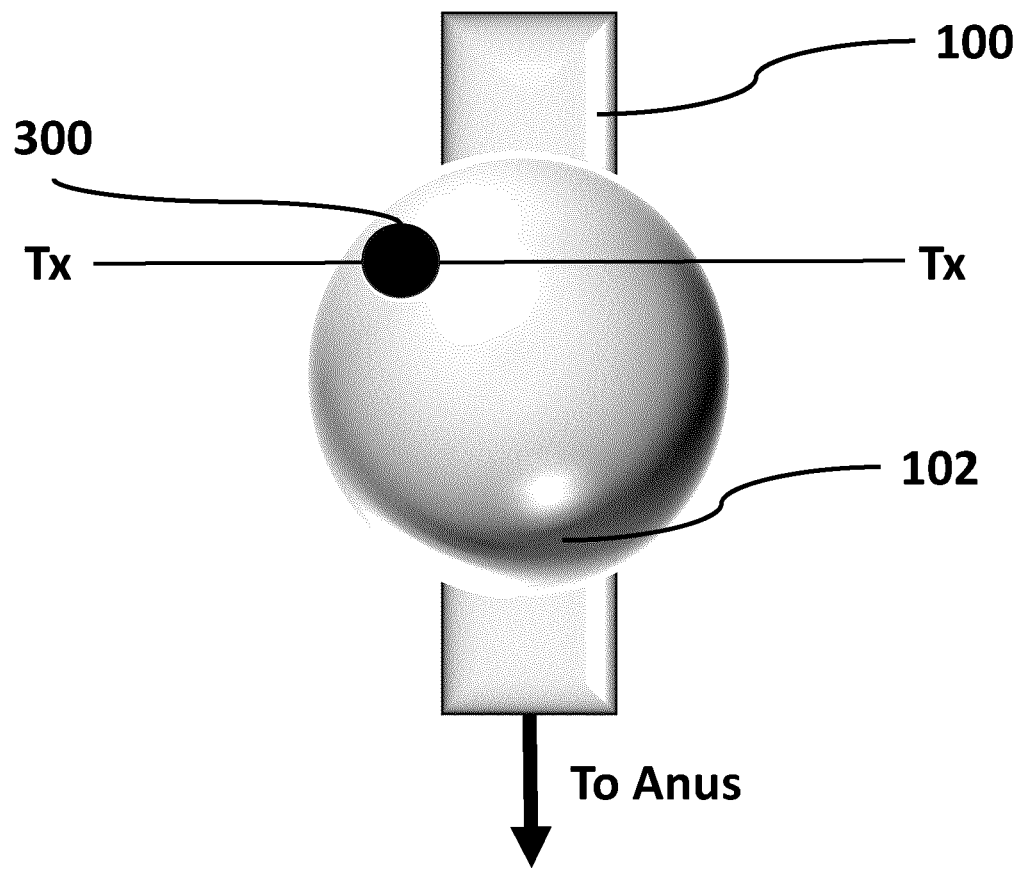
Figure 3B:
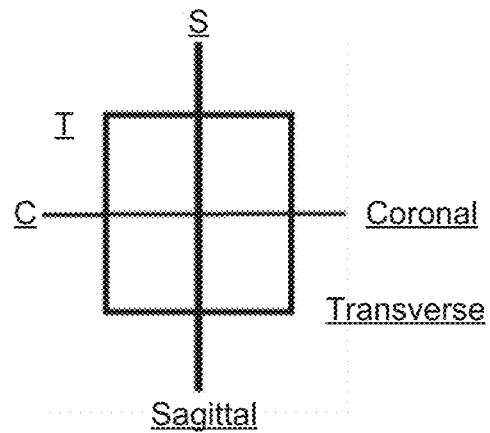
FIG. 3B (SHEET 9/27) is a transverse plane view of the prostate and rectum of FIG. 3A.
Figure 3B:
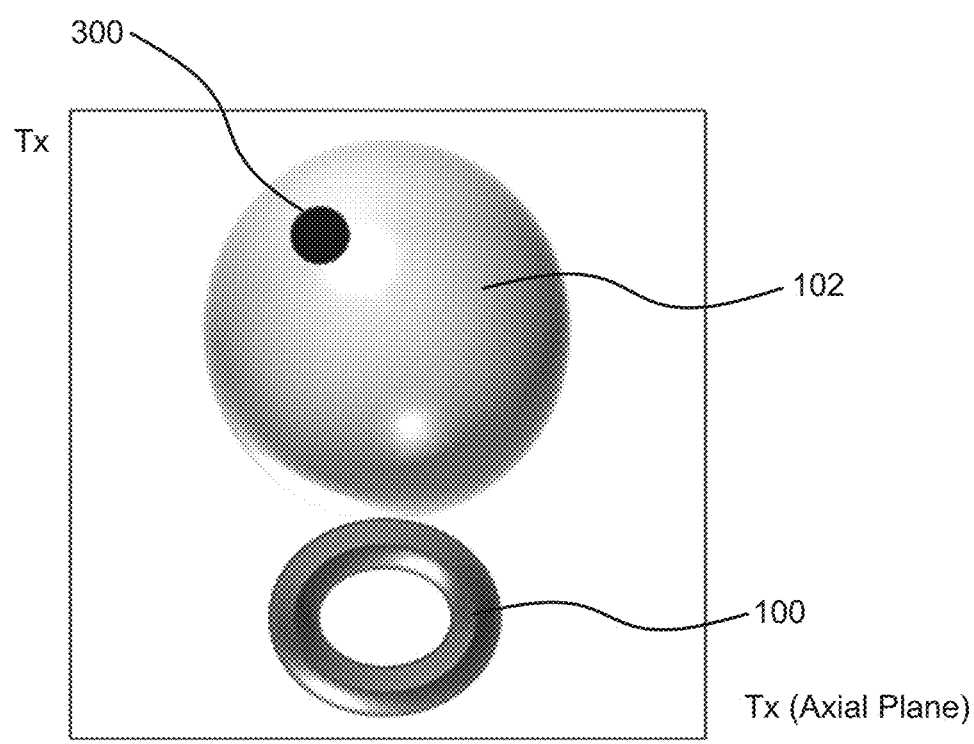

By way of example, FIG. 3A to FIG. 3F depict how MRI imaging fused with ultrasound imaging in the current disclosure might be used to detect a lesion 300 on a prostate 102. In this example FIG. 3A (SHEET 8/27) is a coronal plane representative view of a prostate and rectum, the prostate having a lesion. FIG. 3B (SHEET 9/27) is a transverse plane view of the prostate and rectum of FIG. 3A.

In FIG. 3A and FIG. 3B, the prostate 102 has a lesion 300. In this example, different representative views of a single MRI image of a part of the prostate 102 (including a part of the lesion 300) is taken along the transverse (or axial) axis in FIG. 3A and the transverse (or axial) plane marked by Tx-Tx in FIG. 3B.

Figure 3C:
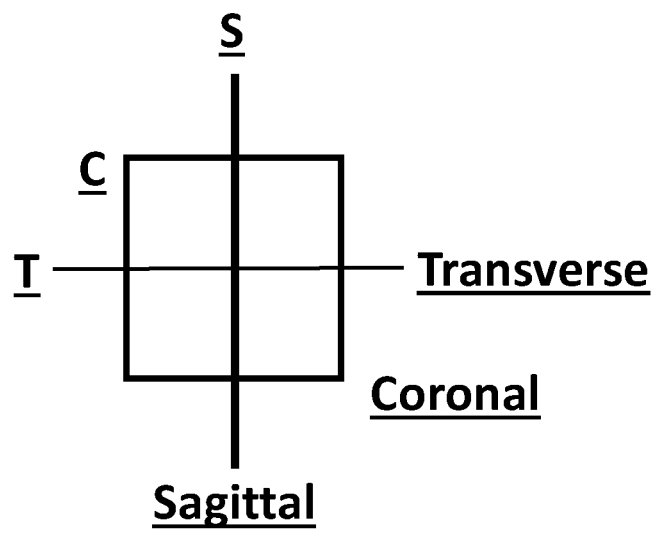
FIG. 3C (SHEET 10/27) is a coronal plane representative view of the prostate and rectum of FIG. 3A.
Figure 3C:
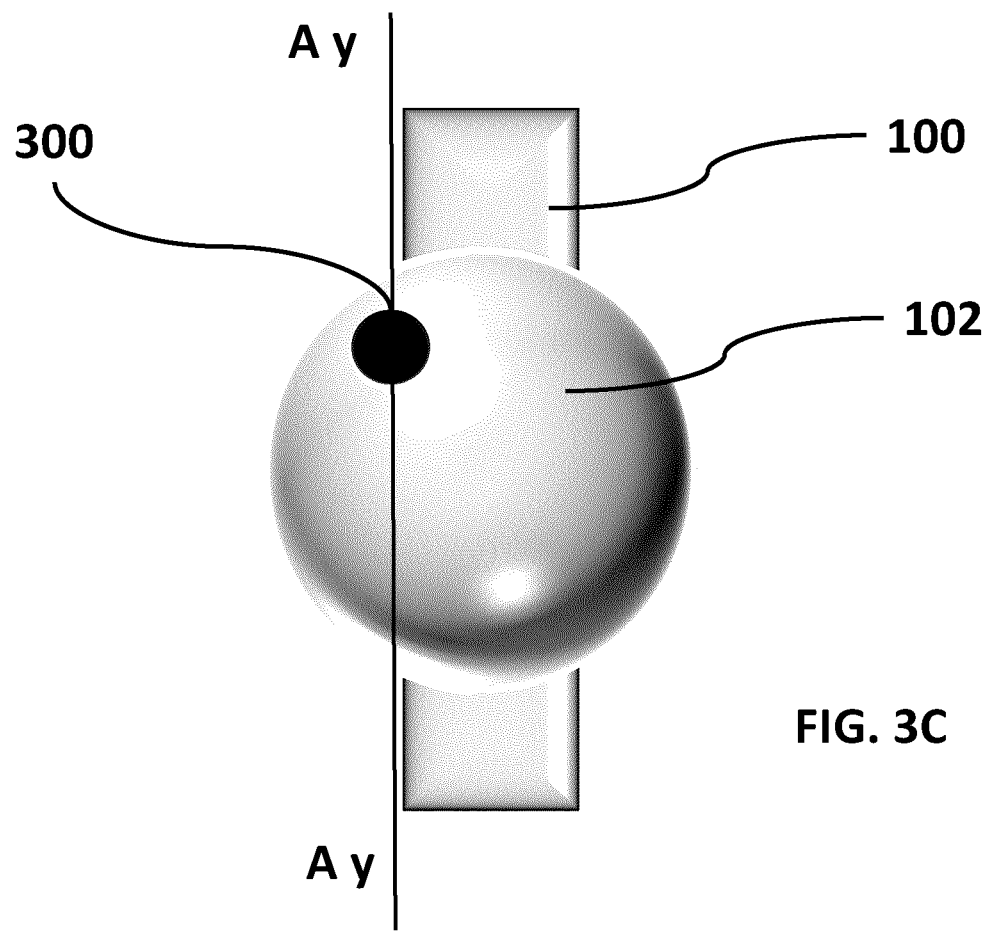
Figure 3D:
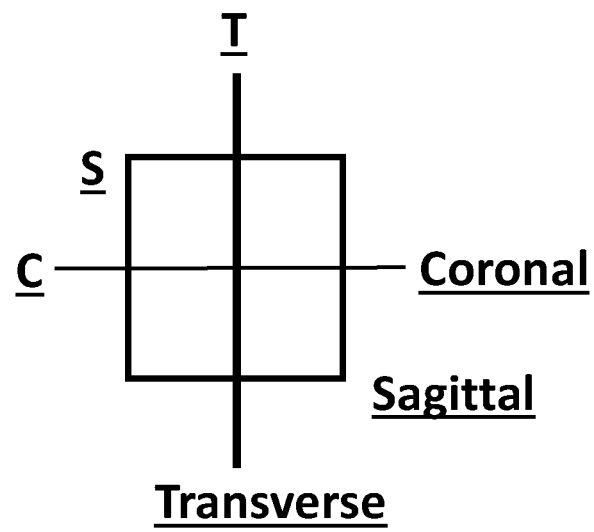
FIG. 3D (SHEET 11/27) is a sagittal plane representative view of the prostate and rectum of FIG. 3A.
Figure 3D:
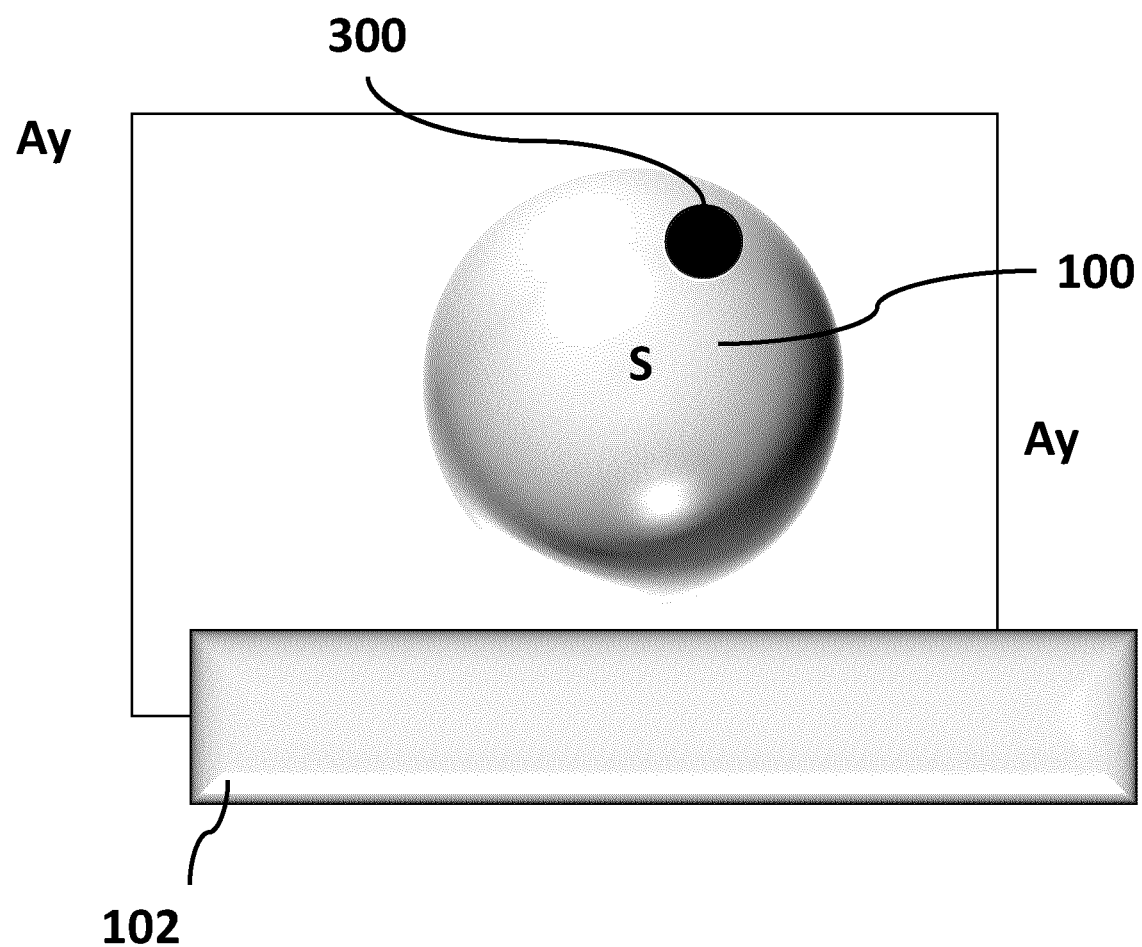

FIG. 3C (SHEET 10/27) is a coronal plane representative view of the prostate and rectum of FIG. 3A. FIG. 3D (SHEET 11/27) is a sagittal plane representative view of the prostate and rectum of FIG. 3A. FIG. 3C and FIG. 3D represent different views of a single MRI image of a part of the prostate 102 (including a part of the lesion 300) that is taken along the sagittal plane marked by Ay-Ay.

Figure 3E:
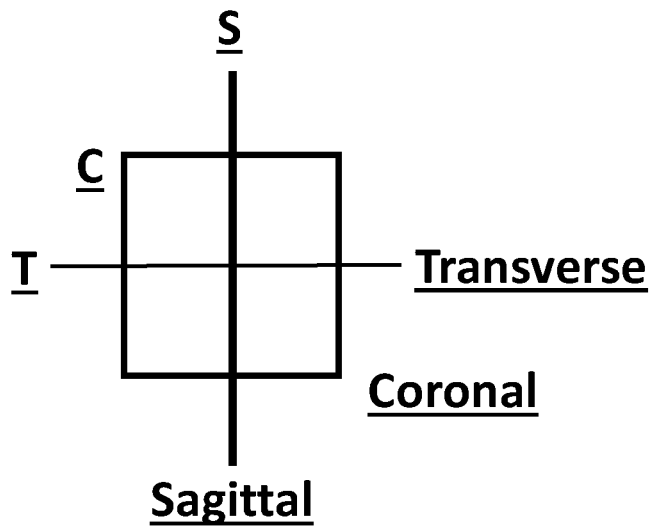
FIG. 3E (SHEET 12/27) is a coronal plane representative view of the prostate and rectum of FIG. 3A.
Figure 3E:
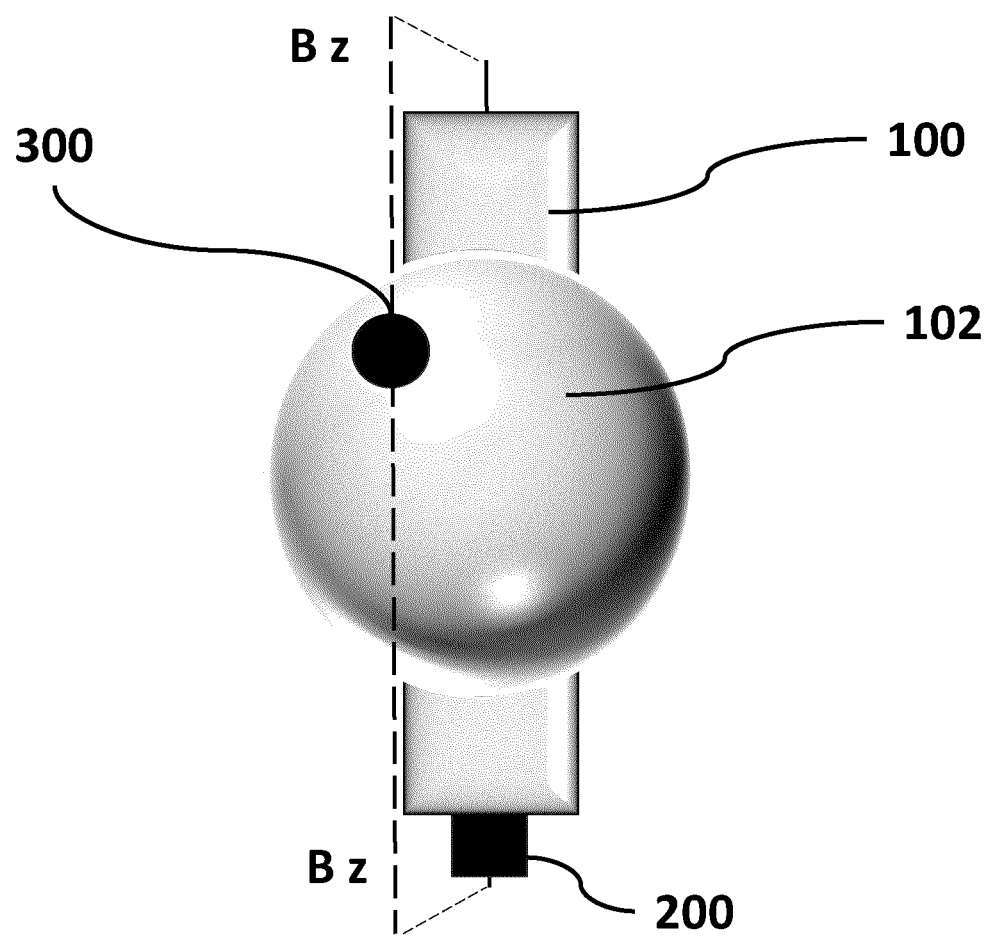
Figure 3F:
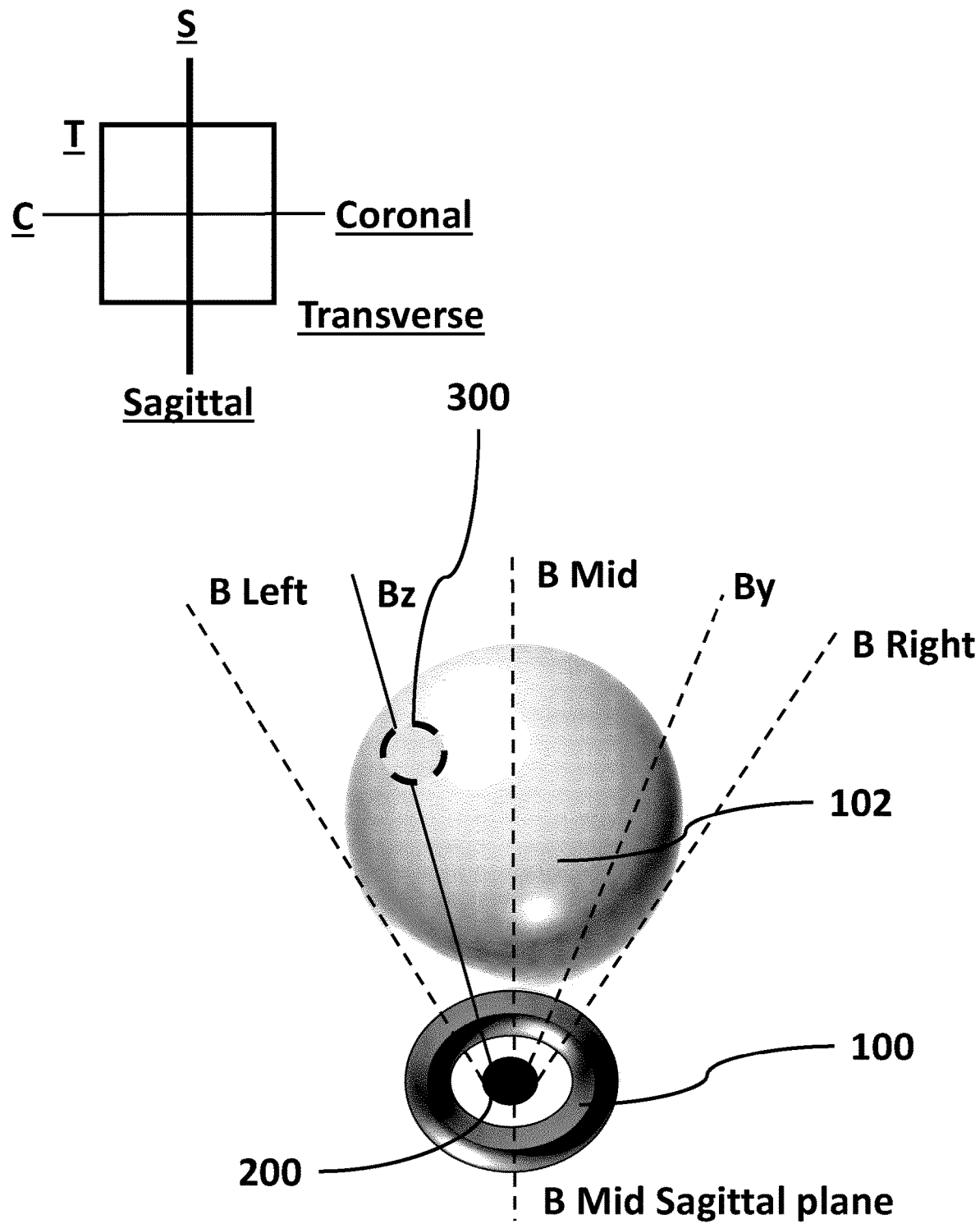
FIG. 3F (SHEET 13/27) is a transverse plane representative view of the prostate and rectum of FIG. 3A.

FIG. 3E (SHEET 12/27) is a coronal plane representative view of the prostate and rectum of FIG. 3A. FIG. 3F (SHEET 13/27) is a transverse plane representative view of the prostate and rectum of FIG. 3A. FIG. 3E and FIG. 3F represent different views of a single ultrasound image of a part of a prostate 102 (including part of the lesion 300) that is taken along the plane marked Bz in FIG. 3E (i.e., a plane that is oblique to the coronal plane) and the axis marked Bz in FIG. 3F.

In contrast to the MRI device, a surgeon or urologist can perform a procedure while simultaneously using the ultrasound imaging device. However, the ultrasound imaging lacks the resolution and fidelity of the MRI images. This makes positively identifying structures such as lesions difficult, at least when compared to MRI images. Fusing the MRI image data with the ultrasound image feed, then, provides the necessary details for a urologist or surgeon to identify lesions in a prostate while also allowing the urologist or surgeon to perform procedures on the prostate.

A skilled person would understand that MRI data uses a Cartesian coordinate system. A skilled person would understand that scale is part of MRI data, that there is a voxel to millimeters scale (mm). This voxel to mm scale allows for the determination of the size of the prostate from the MRI data. In an embodiment, all or a part of the prostate boundary (i.e., an alignment mark) is identified and labelled in the MRI data. For example, in some embodiments the MRI data is marked using DICOM annotation tags to identify lines, points, and regions of interest. These lines, points, and regions of interest are used to identify structures (such as lesions) and landmarks 800 that include, but are not limited to, the border between the rectal wall and prostate in the midline frame of the sagittal series of MRI images. It will be appreciated that any anatomical landmarks 800 that can be consistently visualized between MRI and ultrasound can be marked and used.

In some embodiments the landmark 800 is scaled so that the size of the prostate can be derived from the length of the landmark 800. In this embodiment the size of the prostate can be determined by the length of the landmark 800 since the landmark 800 is scaled.

A skilled person would understand that ultrasound data also has a voxel to millimeters scale.

In an embodiment, the systems and methods may be usable with computed tomography scan, and any imaging modality that provides 3D information. For example, the 3D imaging information may be stored in the Digital Imaging and Communications in Medicine (DICOM) format.

In another embodiment, the systems and methods may be usable with recorded ultrasound and live ultrasound fusion. The use of recorded ultrasound imaging data of a patient's prostate will allow for comparison of the patient's prostate over a period of time. For example, a recording of ultrasound data made presently, may be fused or visually inspected in relation to live ultrasound imaging done a year after the recording. The live ultrasound imaging may also be recorded and used in the future.

Figure 4:
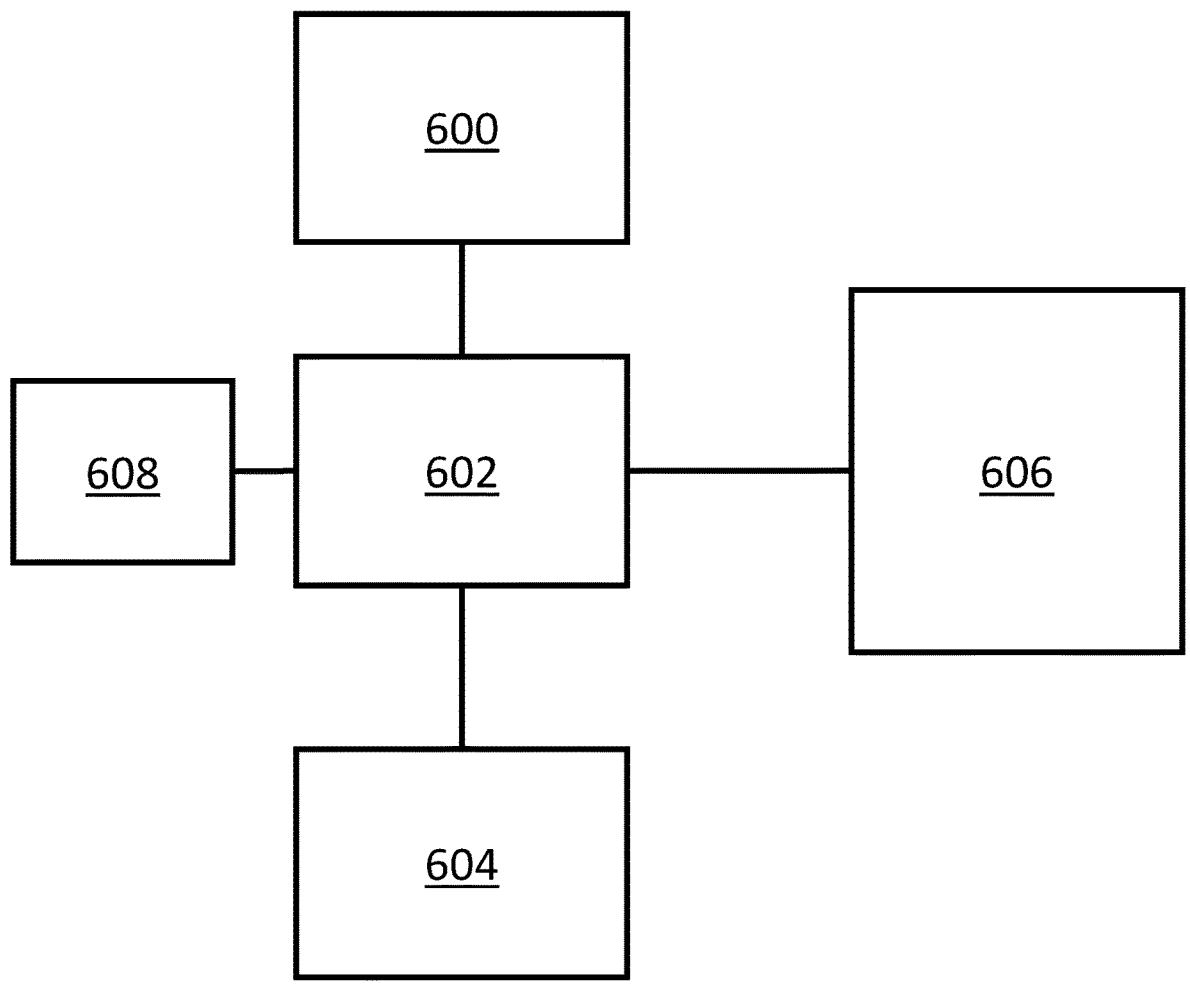
FIG. 4 (SHEET 14/27) is a system diagram of an embodiment of a system.

FIG. 4 (SHEET 14/27) is a system diagram of an embodiment of a system. In this embodiment the system includes a display device 600 for displaying data from the processing unit 602. Data from the processing unit 602 may include, but is not limited to, images and video (e.g. ultrasound scan images/video, and/or MRI images), and UI components. In some embodiments the display device 600 may be responsive to touch. In the embodiments where the display device 600 is responsive to touch this "touchscreen" can also be used, at least in part, as an input device.

In this embodiment the processing unit 602 is configured to accept input from one or more input devices 608; retrieve, store, and process data from the data store 608; display data to the display device 600; and control, operate, and send and receive data from a trans-rectal side-fire ultrasonic transducer probe 606. In some embodiments the processing unit 602 is a personal computer having (at least) a motherboard, a memory, a processing unit, a video processing unit (e.g. internal or external video card), a mass data storage device (e.g. hard disk drive, solid state disk drive), an external data storage device (e.g. a digital video disk player/recorder, a Blu-ray disk player/recorder), a power supply, a network connection device (e.g. Ethernet card and port, a WiFi card and antenna), peripheral connection device and connectors (e.g. USB/USB2/USB3/USB3.1 connectors, Thunderbolt connectors, parallel ports, serial ports, etc.), and any other components associated with a desktop, laptop, or enterprise-class computing device.

In this embodiment the system may have an input device 604. This input device is configured to accept input from a user of the system. Examples can include, but are not limited to, keyboards, mice, touchpads, touchscreen, trackballs, and the like. It will be appreciated that, in embodiments where the display device 600 includes input functionality (e.g., a touchscreen), that the separate input device 604 supplement the input device of the display device 600, or in some embodiments may not be required.

In this embodiment the system includes a trans-rectal side-fire ultrasonic transducer probe. Since side-fire ultrasonic transducer probes are largely constrained to moving in two directions (roll and in/out) fewer tracking components were necessary when compared to an end-fire ultrasonic transducer probe (which have up to 6 degrees of freedom in term of position and orientation). In this embodiment the side-fire ultrasonic transducer probe includes an Inertial Monitoring Unit (IMU) that tracks the roll, pitch, and yaw angle of the side-fire ultrasonic transducer probe. In an embodiment, only the roll angle of the side-fire ultrasound probe is used for alignment and tracking. It will be appreciated that other types of transducer probes (such as end-fire) could be used. Using sensors other than a side-fire transducer probe, however, may require more complex spatial monitoring devices.

In this embodiment, the MRI image and/or report data may be loaded on the processing unit 602 via physical media (e.g. CDs, DVDs, Blu-Ray discs, USB Drives, etc.), over a computer network, or Picture Archiving and Communications Systems (PACS). This MRI image and/or report data can then be used by the processing unit 602 in the merge step, described below. Examples of MRI image and/or report data include, but are not limited to, reports following the PI-RADS (TRADEMARK) guidelines or other generally accepted. MRI reporting formats.

It will be appreciated that the components of the system may be connected via any known communication protocol or connection means. For example, the display device 600 may be connected to the processing unit 602 via an HDMI, VGA, Displayport, wirelessly (via infrared, WiFi, or RF communications), or DVI connection, for example. The input device 604 may be connected to the processing unit 602 via (for example) USB, PS2, serial port, Thunderbolt, or wirelessly (via infrared, WiFi, or RF communications). Similarly, the ultrasonic transducer probe 606 may be connected to the processing unit 602 via (for example) USB, PS/2, serial port, Thunderbolt, wirelessly (via infrared, WiFi, or RF communications), or a high-bandwidth connection protocol.

It will also be appreciated that the system may be contained within a portable enclosure rated for use in a clinical setting such as a hospital or medical office. The portable enclosure is configured to house the components so that the system can be moved from one location to another without having to relocate or reconfigure parts of the system.

In some embodiments portions of the system may be implemented in a cloud computing environment. For instance, in some embodiments, the processing unit and/or data store may be partially or fully implemented in a cloud computing environment. Any remaining parts of the system that cannot easily be implemented in a cloud environment (e.g., the ultrasound probe, display, input, etc.) may then be configured within a portable enclosure.

Referring again to FIG. 4 (SHEET 14/27), in another embodiment a system for visually assisting an operator of an ultrasound system is provided. The system includes a data store 608 for storing a first imaging data of a first prostate using a first coordinate system, the first imaging data marked with a landmark 800 for identifying the first prostate. The system further includes an ultrasound transducer 606 for collecting: live ultrasound image data of a second prostate, and positional information from the ultrasound transducer, including positional information corresponding to an alignment point of the second prostate. The system includes a processing unit 602 for: receiving positional information from the ultrasound transducer corresponding to the alignment point of the second prostate; and transforming the first imaging data of the first prostate from the first coordinate system to a cylindrical coordinate system. The system also includes a display device 600 for displaying both the transformed image and the ultrasound image data corresponding to the positional information of the ultrasound transducer.

The system may also include an input device 600 for receiving a first imaging data of a first prostate using a first coordinate system, the first imaging.

Referring again to FIG. 4 (SHEET 14/27), in yet another embodiment a system for visually assisting an operator of an ultrasound system is provided. This embodiment includes a data store 608 for storing a 3D model prostate imaging data, the 3D model prostate imaging data in a cylindrical coordinate space. The system further includes an ultrasound transducer 606 for collecting: live ultrasound image data of a second prostate; and positional information from the ultrasound transducer, including positional information corresponding to an alignment point of the second prostate. Aa processing unit 602 is included for: receiving positional information from the ultrasound transducer corresponding to the alignment point of the second prostate; and transforming the 3D model prostate imaging data based on the received positional information corresponding to the alignment point of the second prostate. A display device 600 is included for displaying both the transformed image and the ultrasound image data corresponding to the positional information of the ultrasound transducer.

In some embodiments the system may further include an input device 600 for receiving a region of interest for the 3D model prostate.

Figure 5:
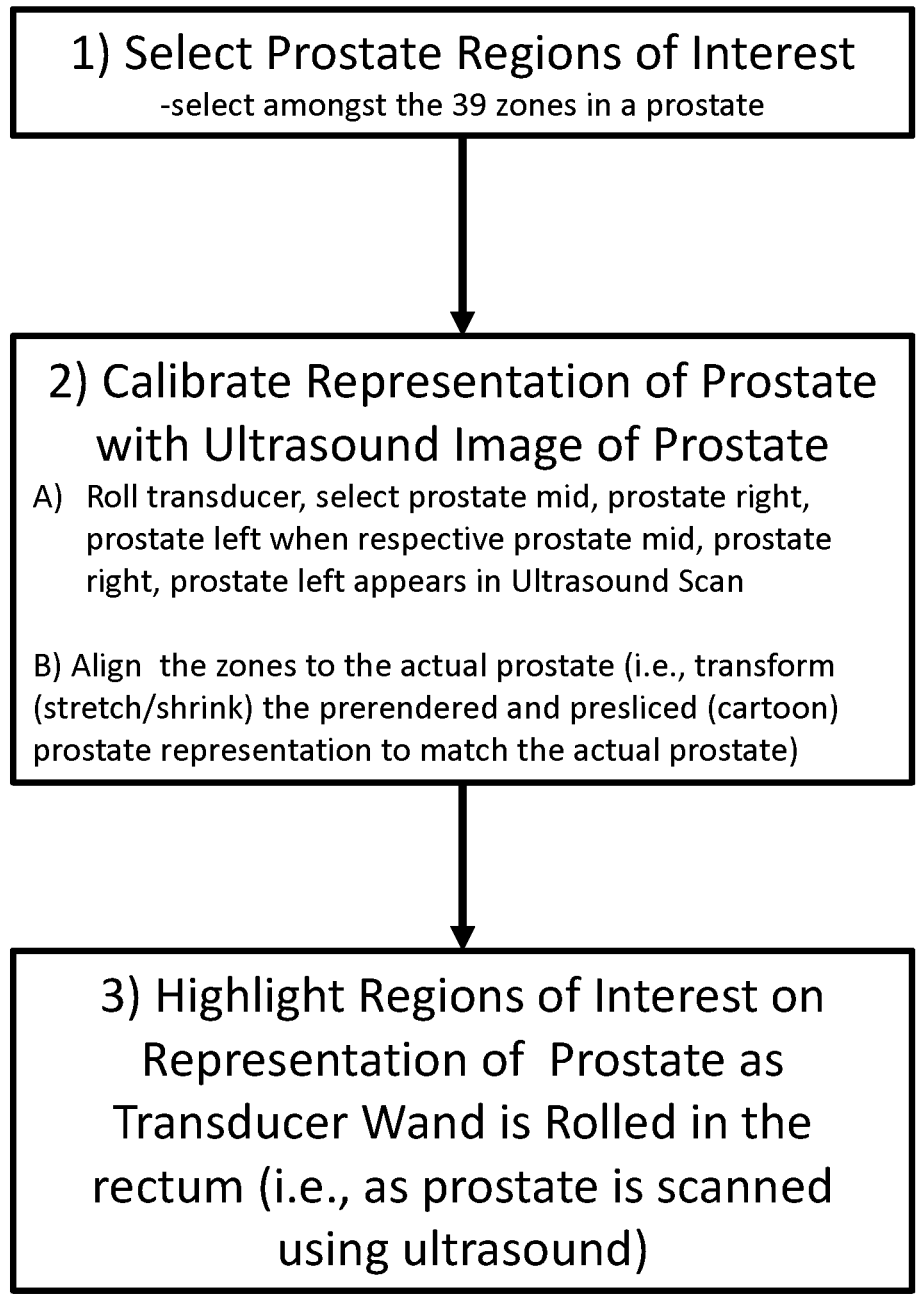
FIG. 5 (SHEET 15/27) is a flow chart depicting an embodiment workflow.

FIG. 5 (SHEET 15/27) is a flow chart depicting an embodiment workflow. In this workflow a user first selects, on an input device of an ultrasound imaging device, one or more regions of interest to investigate in a prostate. These regions of interest may include, but are not limited to, the zones in the zone classification system (i.e., the 39 zones). In some instances, the urologist or surgeon may consult a MRI report when selecting a region of interest to investigate. MRI reports can include, but are not limited to, reports following the PI-RADS (TRADEMARK) guidelines. The urologist or surgeon may also simply select regions to investigate.

Figures 6A, 6B:
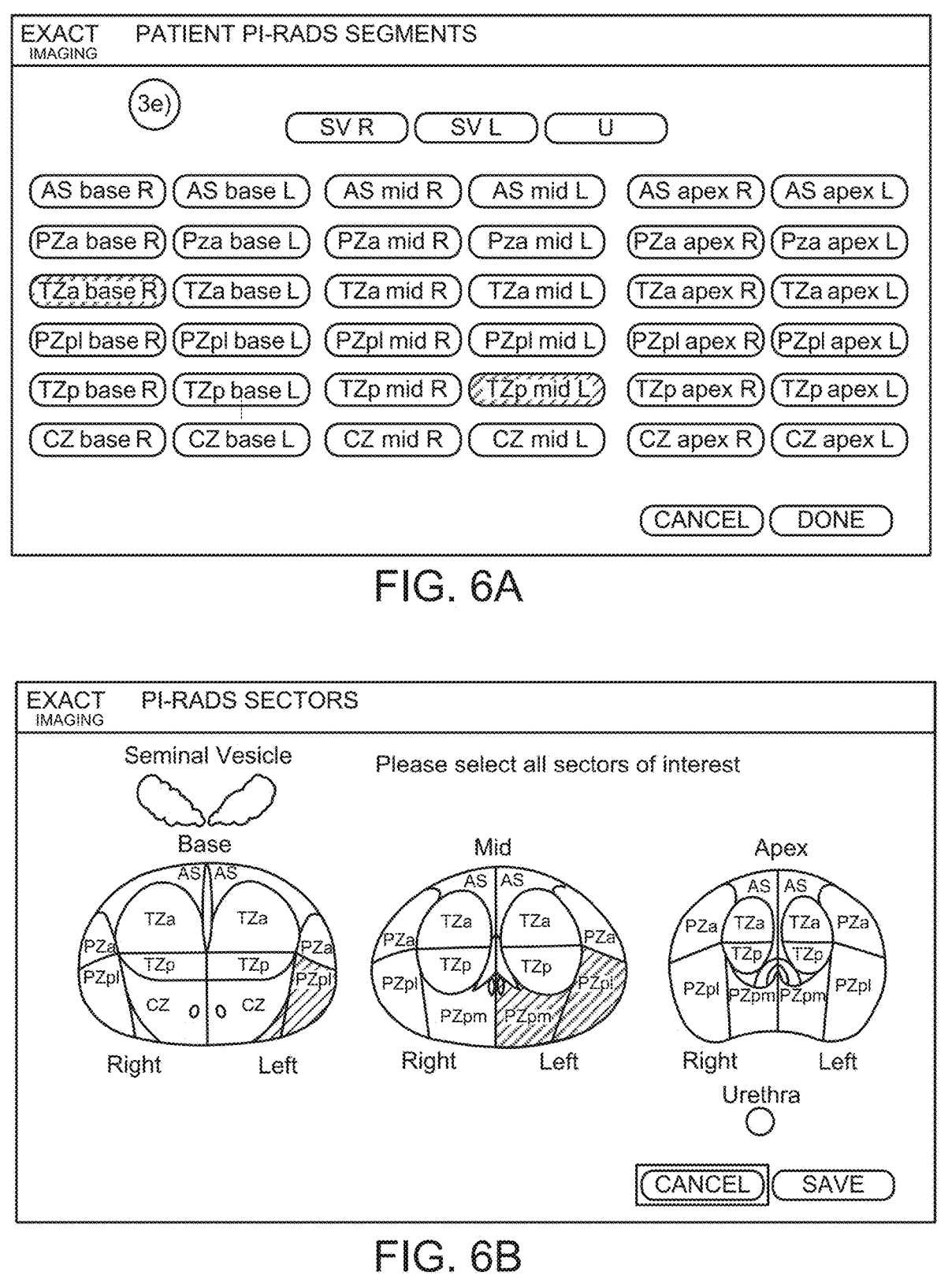

FIG. 6A (SHEET 16/27) is an embodiment partial user interface (UI) for the workflow of FIG. 5. This partial UI displays the zones of a prostate in a selectable table format. The urologist or surgeon (or the assistant) may select the regions by using the input device of the ultrasound imaging device. FIG. 68 (SHEET 16/27) is an alternate embodiment partial UI for the workflow of FIG. 5. Instead of the selectable table format, the alternate partial UI of FIG. 6B displays the zones of the prostate as an image, with the respective zones of the prostate mapped on the images.

Again, the urologist or surgeon (or the assistant) may select the regions by using the input device of the ultrasound imaging device.

Figure 7:
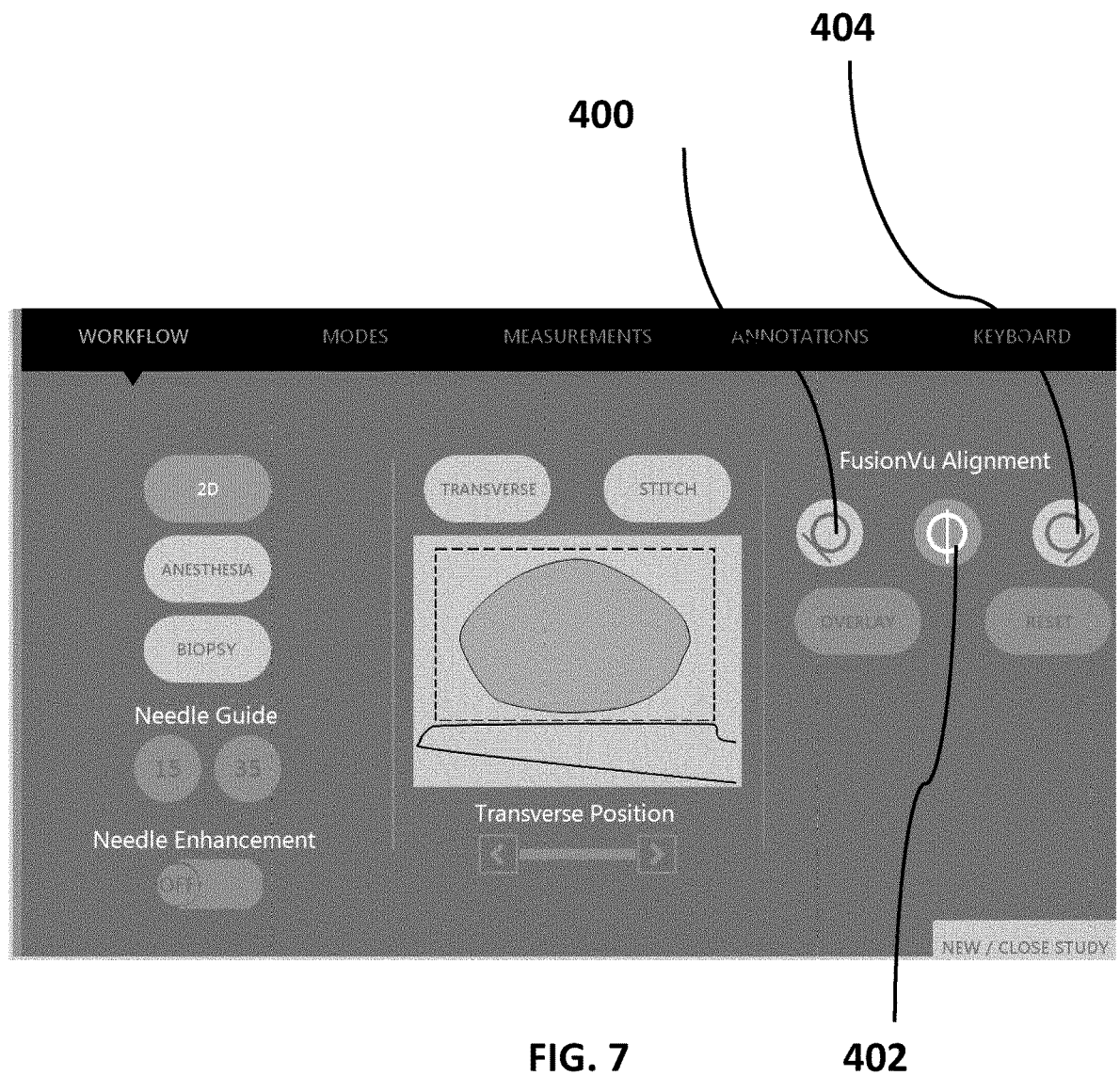
FIG. 7 (SHEET 17/27) is an embodiment partial UI for the workflow of FIG. 5.

FIG. 7 (SHEET 17/27) is an embodiment partial UI for the workflow of FIG. 5. Once the regions of interest have been selected the urologist or surgeon (or an assistant) performs an overview scan of the prostate using a side-fire trans-rectal ultrasound transducer probe. While performing the overview scan, the urologist or surgeon (or an assistant) marks (via the input device of the ultrasound imaging device) the left edge of the prostate, the right edge of the prostate, and the mid-line of the prostate as the ultrasound scan reaches the respective left edge, right edge, and mid-line of the prostate. In this example UI, the urologist or surgeon (or an assistant) would click on the left calibration button 400 once the left edge of the prostate is displayed on the display device of the ultrasound imaging device. The urologist or surgeon (or an assistant) would click on the middle calibration button 402 once the mid-line of the prostate is displayed on the display device of the ultrasound imaging device. Finally, the urologist or surgeon (or an assistant) would click on the right calibration button 404 once the right edge of the prostate is displayed on the display device of the ultrasound imaging device.

Once the alignment information has been entered into the ultrasound imaging device, the ultrasound imaging device transforms a pre-rendered 3D representation of the prostate so that its dimensions and characteristics are similar to that of the actual scanned prostate. In this example the 3D representation of the prostate is stretched/shrunk, or scaled, to better align with the size of the actual prostate.

In this embodiment the 3D representation of the prostate is pre-sliced so as to speed up the transformation process. That is, since the "roll arc" of a side-fire ultrasonic transducer probe in a rectum is known, the 3D representation of the prostate can be mapped to specific roll/zone angles of the ultrasonic transducer probe prior to knowing the actual size of the prostate being investigated. These "pre-slices" can then be transformed (stretched/shrunk, or scaled) as required.

In an embodiment, the 3D representation of the prostate is built as a 3D mesh model. Utilities for building 3D mesh models include, but are not limited to, Computer Aided Design software, BLENDER (TRADEMARK), UNITY (TRADEMARK), etc. Once a 3D representation of the prostate has been built, the mesh is "sliced" into "fan" representations that correspond, at least in part, to the ultrasound images that would be captured using the device (such as, for example, the "fan" slices as described in FIG. 20).

Figure 8A:
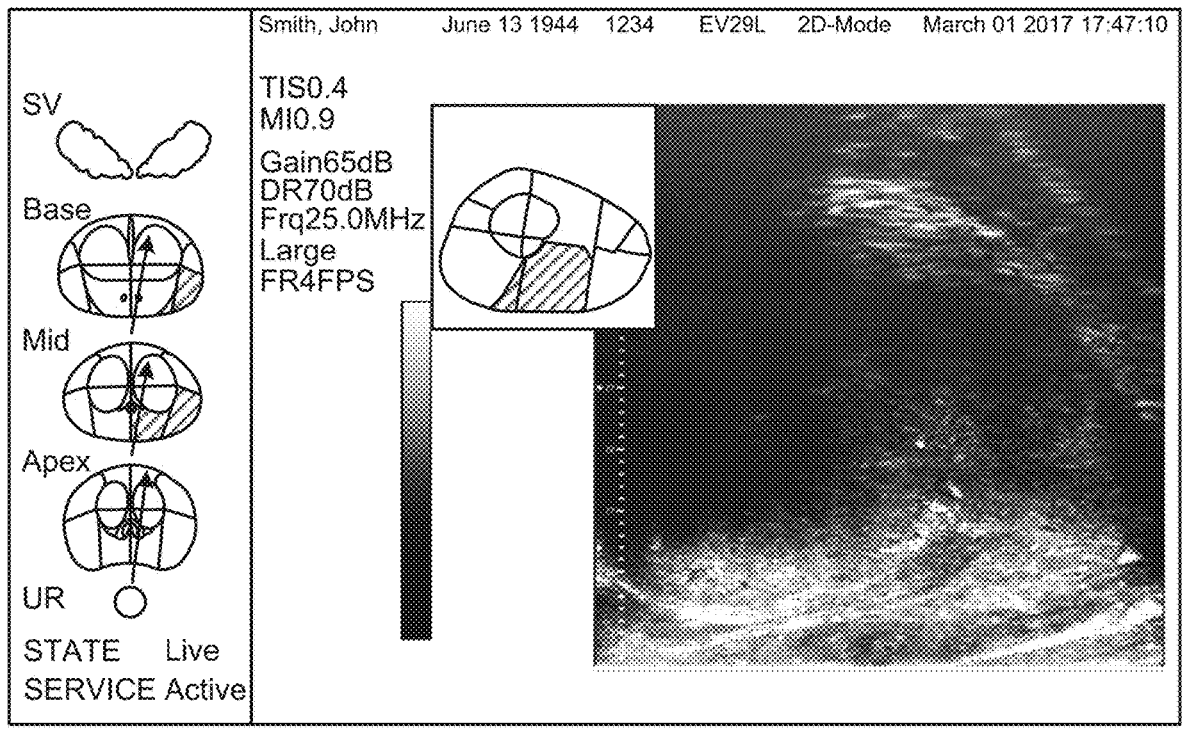
FIG. 8A (SHEET 18/27) is an embodiment partial UI for the workflow of FIG. 5.
Figure 8B:
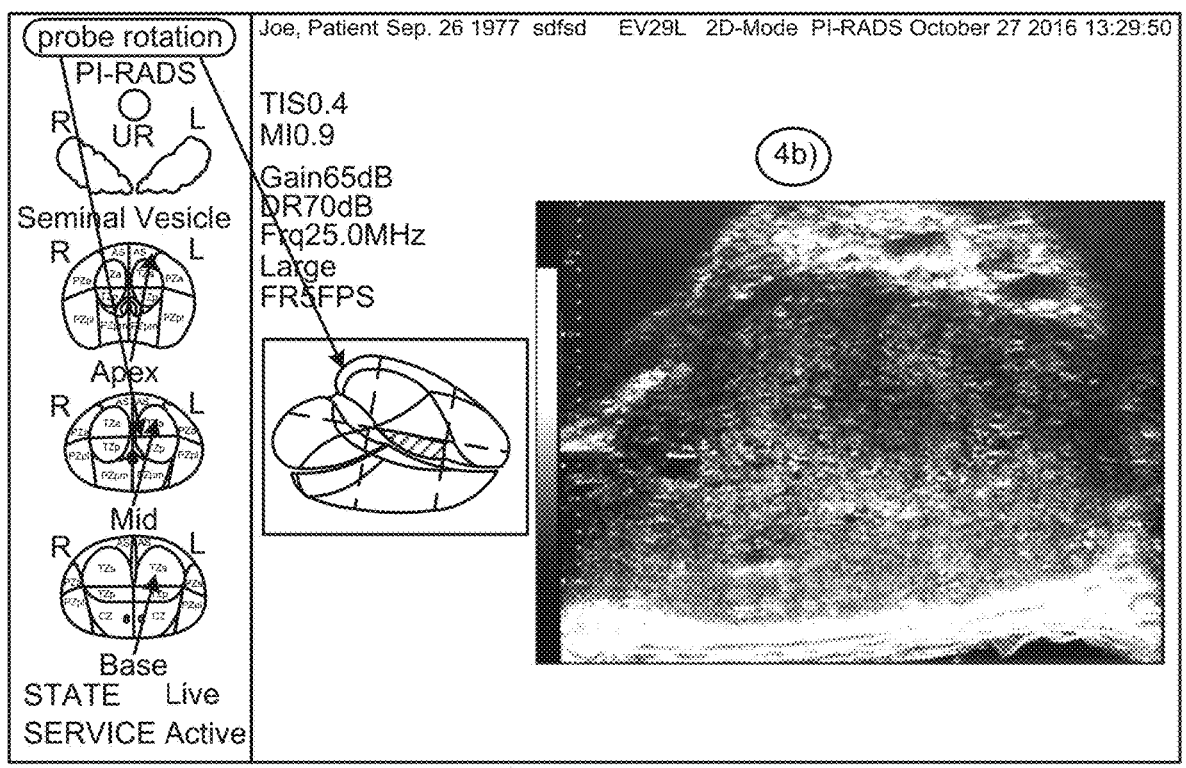
FIG. 8B (SHEET 18/27) is an alternate embodiment partial UI for the workflow of FIG. 5.

Once the remapping and transformation is complete the urologist or the surgeon (or the assistant) can use the ultrasound imaging device to scan the regions of interest. Examples of how the 3D representation of the prostate (including zone information) is displayed simultaneously with the ultrasound image is provided in FIG. 8A and FIG. 8B. FIG. 8A (SHEET 18/27) is an embodiment partial UI for the workflow of FIG. 5. FIG. 8A shows the representation of the prostate being displayed in an overlay format. FIG. 8B (SHEET 18/27) is an alternate embodiment partial UI for the workflow of FIG. 5. FIG. 8B shows the representation of the prostate being displayed in a side-by-side format.

In this example UIs depicted in FIG. 8A and FIG. 8B, as the ultrasound transducer probe is rolled in the rectum the corresponding zone in the prostate is displayed in the representation of the prostate on the left side of the screen. As the urologist or the surgeon (or the assistant) scans different areas of the prostate, the corresponding zone will be highlighted in the representations of the prostate.

In an embodiment, the zones selected by the user will be highlighted as the transducer probe is rolled/rotated in the rectum. The image slice shown is determined according to the following function:

$$I=M/2\times(\theta a/\alpha+1)$$

$$\theta a=(\theta-\theta m)/(\theta r-\theta m)\times\alpha \text{ [when } \theta-\theta m \text{ is positive]}$$

$$\theta a=(\theta-\theta m)/(\theta m-\theta l)\times\alpha \text{ [when } \theta-\theta m \text{ is negative]}$$

Where:
I—image index (0 to M in the fan image series)
$\theta$—the probe rotation angle
$\theta a$—the aligned probe rotation angle
$\theta m$—the probe rotation angle at mid-line
$\theta l$—the probe rotation angle at leftmost (ccw) edge of prostate (patient right)
$\theta r$—the probe rotation angle at rightmost (cw) edge of prostate (patient left)
M—number of images minus 1 (even number)
$\alpha$—the fan half angle (fan spans $-\alpha$ to $\alpha$)

Figure 9:
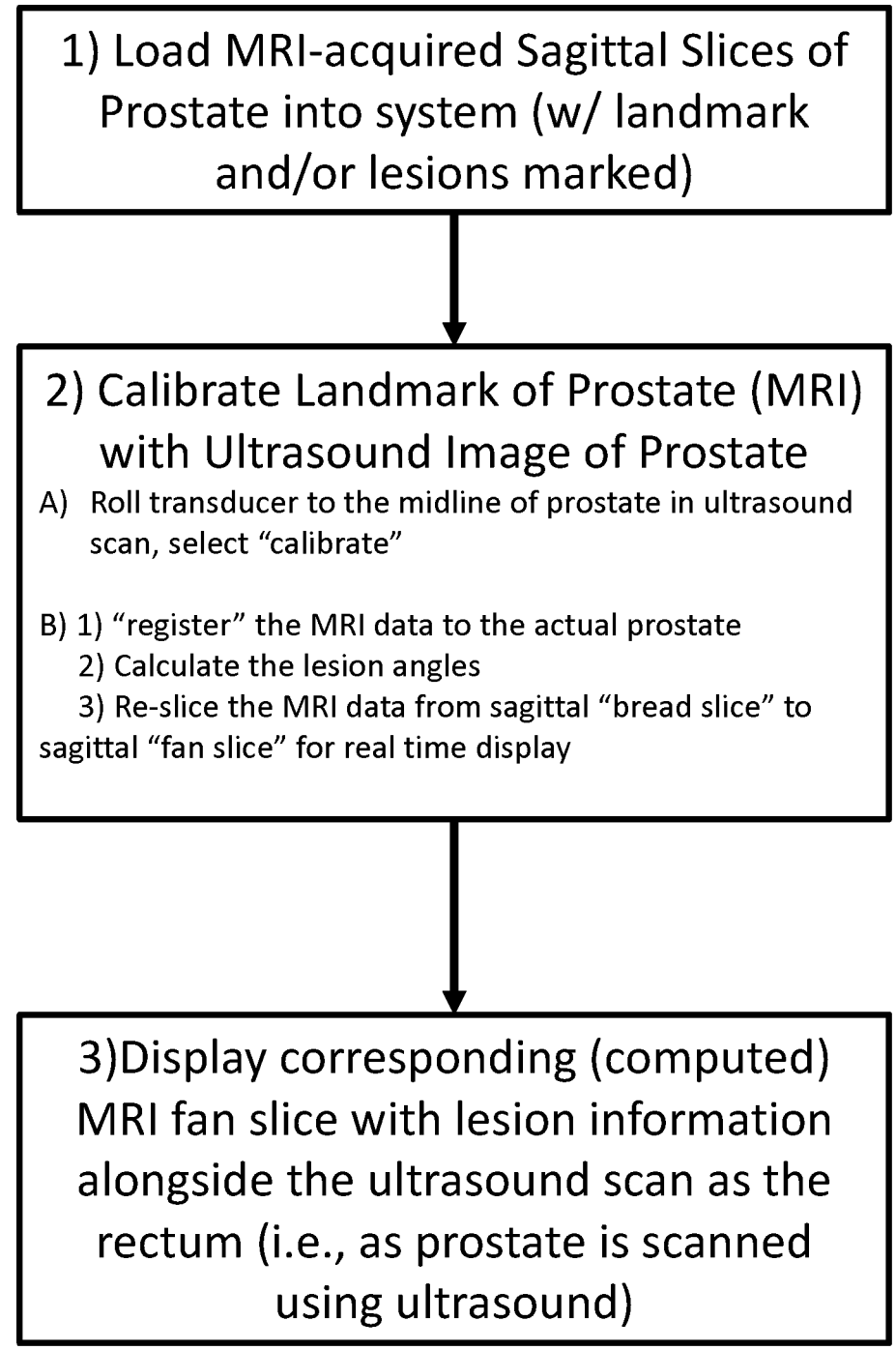
FIG. 9 (SHEET 19/27) is a flow chart depicting an alternate embodiment workflow.

FIG. 9 (SHEET 19/27) is a flow chart depicting an alternate embodiment workflow. In this example previously captured MRI image and/or report data is loaded into the processing unit 602 of the system so that it may be remapped and used in the simultaneous display of MRI image and/or report data and ultrasound image data.

Figure 10A:
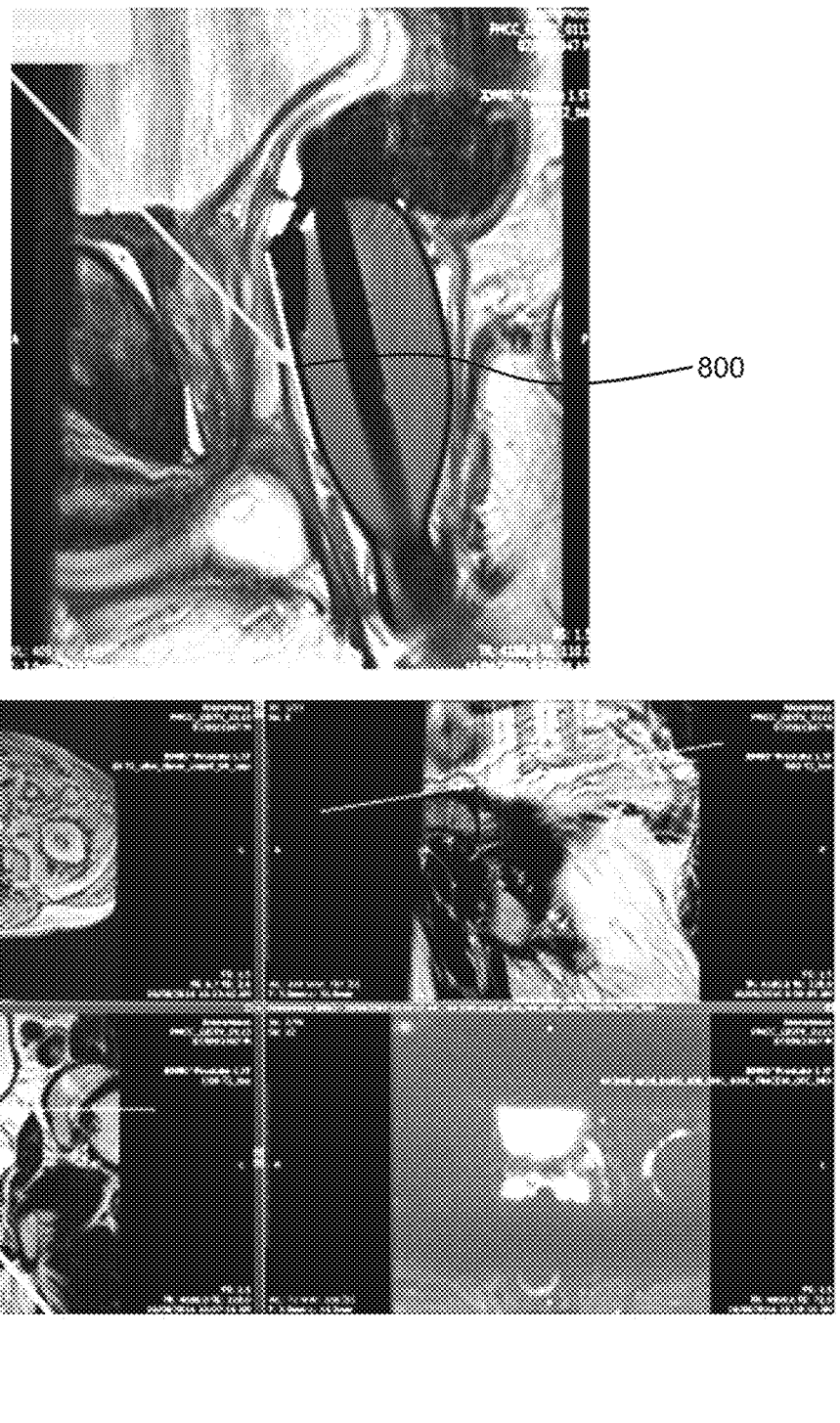
FIG. 10A (SHEET 20/27) depicts example MRI images having an identified landmark and identified lesions.

FIG. 10A (SHEET 20/27) depicts example MRI images and/or report data that might be loaded into the processing unit 602. This data may include identified landmark 800 and identified lesions 802. The MRI images and/or report should contain a landmark 800 "marking" that identifies a structural component in the prostate region with which the system can calibrate and/or orient the ultrasound images. It will be appreciated that the landmark 800 could be any clearly defined body structure that would be identifiable on both an MRI image and an ultrasound image. This can include, but is not limited to, a rectal wall, an edge of a prostate, a midline of a prostate, etc.

Referring again to FIG. 9, in this embodiment the system is configured to accept at least sagittal MRI images of the prostate. In other embodiments, transverse or coronal MRI images of the prostate may also be accepted in place of, or in addition to, the sagittal MRI images.

Figure 10B:
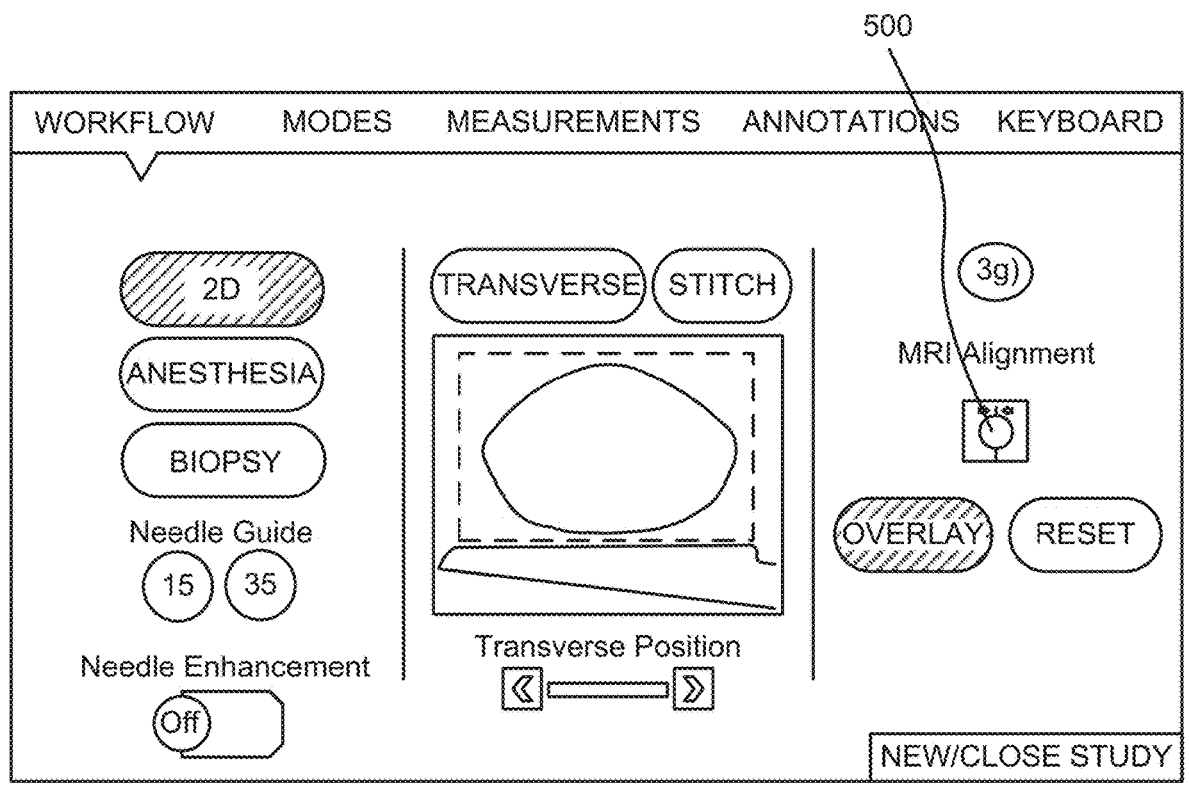
FIG. 10B (SHEET 21/27) depicts an embodiment partial UI for the workflow of FIG. 9.

FIG. 10B (SHEET 21/27) is an embodiment partial UI for the workflow of FIG. 9. Once the MRI image and/or report data has been loaded into the processing unit 602, the urologist, surgeon, or an assistant rolls the ultrasound transducer so that the mid-line of the prostate is in view and then selects the mid-line calibration button on the system. In this example, as the urologist or surgeon (or an assistant) performs an overview scan of the prostate using a side-fire trans-rectal ultrasound transducer probe, the urologist or surgeon (or an assistant) inputs the one or more alignment markers as these markers are displayed on the display device 600. In this example UI, the urologist or surgeon (or an assistant) would click on the MRI Calibration Button 500 once the mid-line of the prostate is displayed on the display device of the ultrasound imaging device.

Once the mid-line of the prostate is known, the processing unit "re-slices" the MRI image data so that the MRI image data corresponds to ultrasound image (or video) data. In the case where the MRI images and/or report data consist of sagittal MRI image data, the processing unit 602 is configured to remap the sagittal MRI image data to "fan-shaped"

images that correspond to the ultrasound imaging data being captured by the system. In this embodiment the processing unit 602 uses the landmark 800 information in the MRI images and/or report data, in addition to the mid-line calibration information, to orient and calibrate the transformation. In another embodiment, the transforming (reslicing) of the MRI image data to ultrasound image (or video) data may be completed on another computing system before it is used for improving performance by reducing processing time.

In an embodiment the MRI sagittal slices will be transformed/remapped by resampling the voxels (3D pixels) in fan planes arranged by rotating around the line annotation axis (drawn by the radiologist) at regular angular intervals (i.e. 2α/M). This results in a series of fan images.

The processing unit 602 may also be configured to calculate lesion angles. In an embodiment, the MRI lesion coordinates will be transformed/remapped by placing each lesion in the nearest fan slice sample point. Depending on the size of the lesion, the lesion may span across multiple fan slices. A skilled person would understand that the angles between fan slices are consistent but the fan slices go from narrow to wider.

Figure 10C:
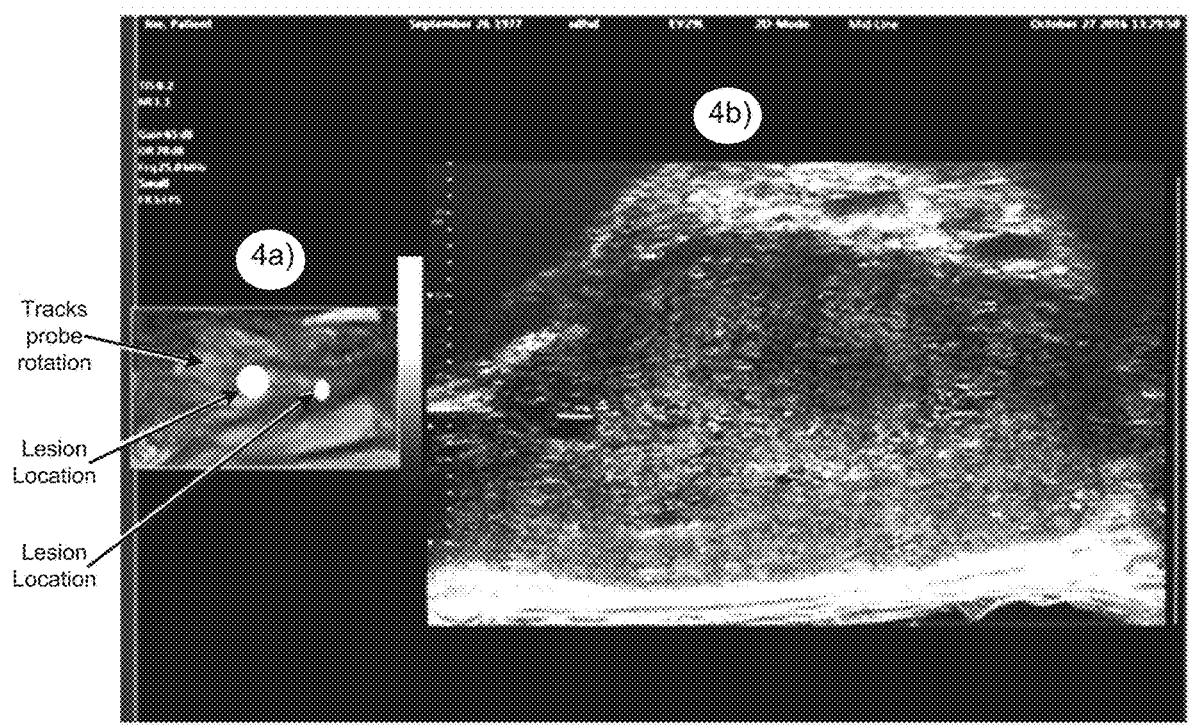
FIG. 10C (SHEET 22/27) depicts an embodiment partial UI for the workflow of FIG. 9.
Figure 10D:
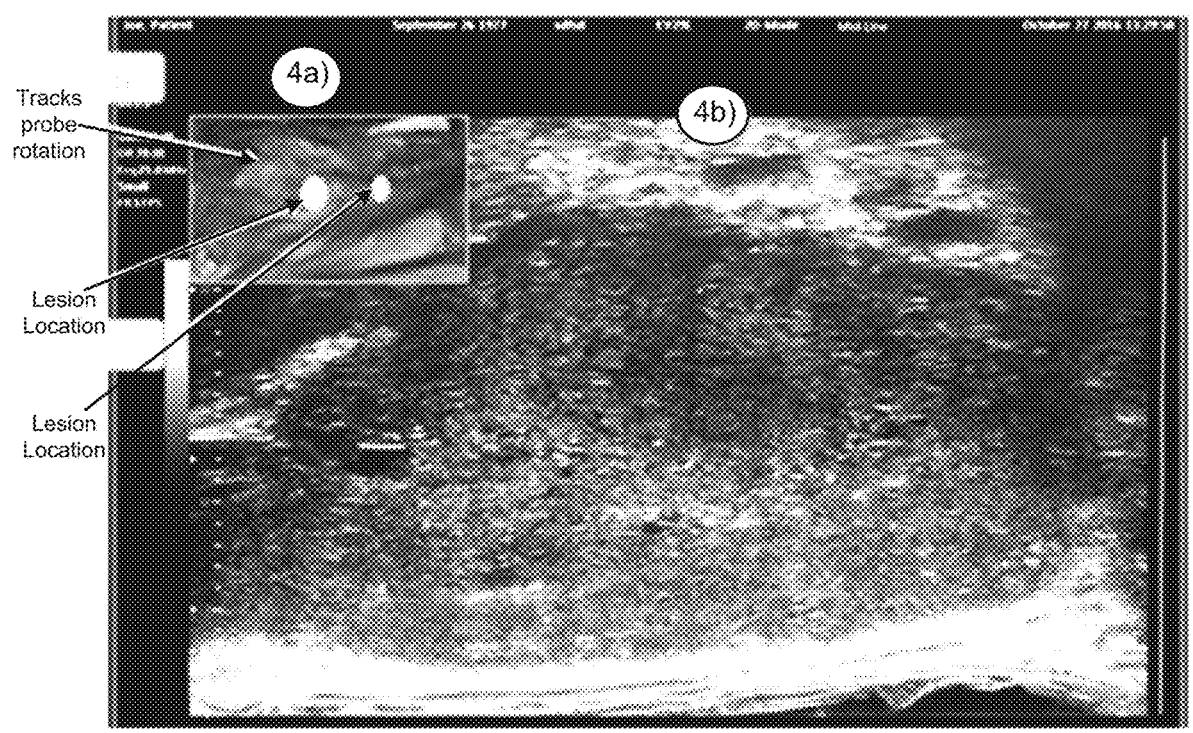
FIG. 10D (SHEET 23/27) depicts an embodiment partial UI for the workflow of FIG.

FIG. 10C (SHEET 22/27) is an embodiment partial UI for the workflow of FIG. 9. FIG. 10D (SHEET 23/27) is an embodiment partial UI for the workflow of FIG. 9. Once the remapping is complete the urologist or the surgeon (or the assistant) can use the ultrasound imaging device to scan the area of interest, and the corresponding MRI data will be displayed simultaneously. FIG. 10C and FIG. 10D provide two different examples of how the MRI image and ultrasound image might be simultaneously displayed. FIG. 10C is an embodiment partial UI for the workflow of FIG. 9. 10C shows the corresponding re-sliced MRI image displayed in a side-by-side format. FIG. 10D is an alternate embodiment partial UI for the workflow of FIG. 9. FIG. 10D shows the corresponding re-sliced MRI image displayed in an overlay format.

In an embodiment the MRI image that will be displayed is determined by the following function:

$$I = M/2 \times (\theta a/\alpha + 1)$$

$$\theta a = \theta - \theta m$$

Where:
I—image index (0 to M in the fan image series)
θ—the probe rotation angle
θa—the aligned probe rotation angle
θm—the probe rotation angle at mid-line
M—number of images minus 1 (even number)
α—the fan half angle (fan spans −α to α)

In the example UIs depicted in FIG. 10C and FIG. 10D, as the ultrasound transducer probe is rolled in the rectum the corresponding re-sliced MRI image is displayed in the representation of the prostate on the left side of the screen. As the urologist or the surgeon (or the assistant) scans different areas of the prostate, the corresponding re-sliced MRI image will be updated. In the embodiment where lesions are also tracked, lesion information is also be displayed on the re-sliced MRI image. The lesion information may also be highlighted, outlined, etc. for improved visibility.

A urologist or surgeon can then compare the re-sliced MRI image with the ultrasound image when performing the ultrasound scan. This is especially useful in biopsy scenarios—the urologist or surgeon can determine whether the region being examined using ultrasound corresponds to the lesion information being displayed on the MRI image. The urologist or surgeon can then guide a biopsy probe or needle to the area of interest and take a sample.

Figure 11:
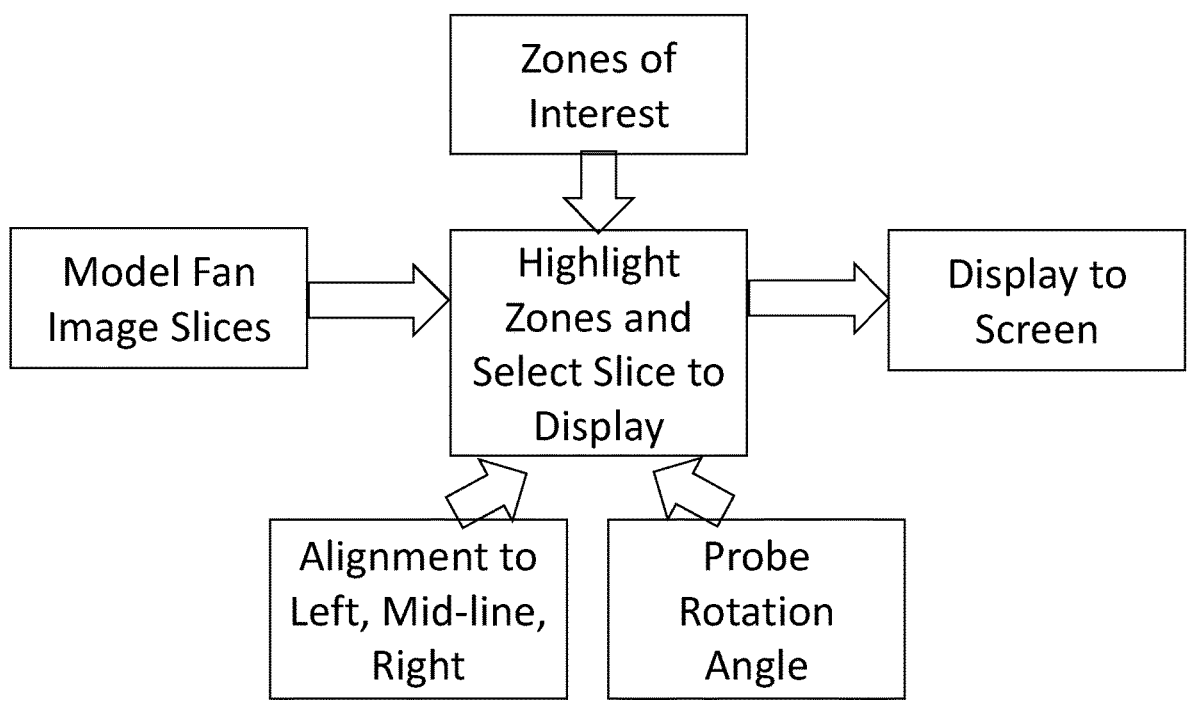
FIG. 11 (SHEET 24/27) depicts an alternate embodiment of Workflow A (workflow A2).

Referring now to FIG. 11 (SHEET 24/27), an alternate embodiment of Workflow A (workflow A2) is provided. In this embodiment the system accepts, as input, the zones of interest, the model fan image slices (that were previously rendered), alignment data corresponding to the actual left, mid-line, and right of the prostate, and the current rotation angle of the ultrasonic transducer probe. Once the alignment information has been acquired, the Model Fan Image Slices can be remapped and/or transformed so that the representation of the prostate is similar to the actual prostate. The processing unit is then configured to determine the zones to highlight (the zones corresponding to the zones of interest) and which model fan image slice to display based on the probe rotation angle. The 3D model of the prostate does not have an absolute scale. Therefore the left, mid, and right alignment scales the 3D model to the size of the prostate being imaged by the ultrasound probe.

Figure 12:
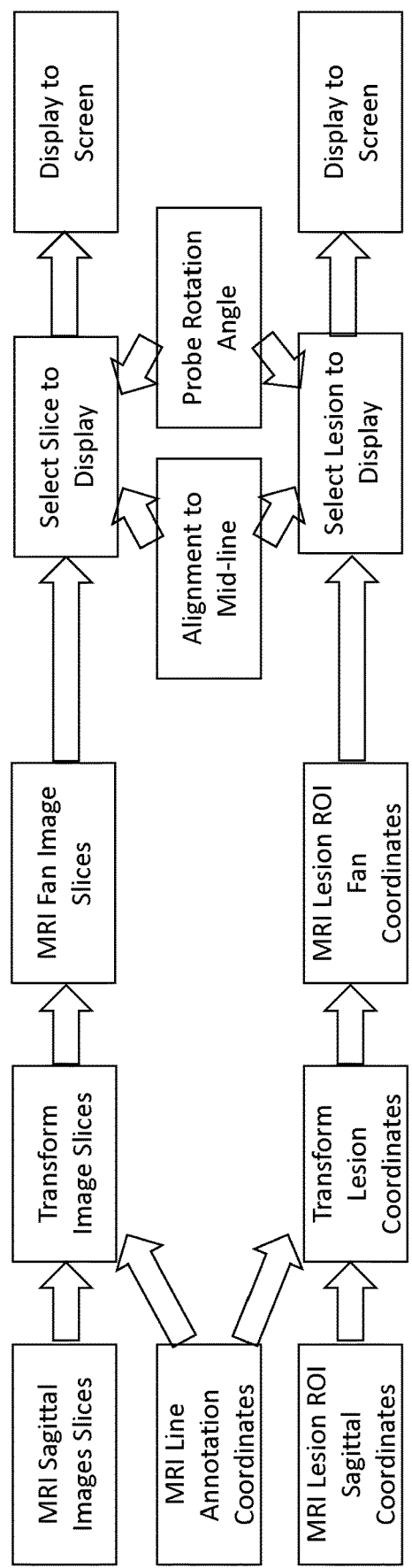
FIG. 12 (SHEET 25/27) depicts an alternate embodiment of Workflow B (workflow B2).

Referring now to FIG. 12 (SHEET 25/27), an alternate embodiment of Workflow B (workflow B2) is provided. In this embodiment the system accepts, as input, MRI Sagittal Image Slices, MRI Line Annotation Coordinates, and MRI Lesion Region of Interest (ROI) Sagittal Coordinates. Once this information has been received, the system transforms/remaps the Sagittal Images Slices using the MRI Line Annotation Coordinates as guides. The result of this transformation/remapping is the MRI Fan Image Slices. Similarly, the system transforms/remaps the MRI Lesion ROI Sagittal Coordinates using the MRI Line Annotation Coordinates as guides. The result of this transformation/remapping is the MRI Lesion ROI Fan Coordinates, which map, at least in part, the MRI Lesion ROI on the MRI Fan Image Slices. In another embodiment, any MRI data set can be used as an input. A skilled person would know how to transform an MRI data set into various planar views or slices.

Once the alignment to the prostate mid-line has been input into the system (in this example, by a user of the system), the Probe Rotation Angle determines, at least in part, which Fan Slice and/or Lesion ROI to display. This information is then displayed on the screen of the device so that a user/urologist/surgeon may refer to them as the procedure is performed.

It will be understood that as the frequency of the ultrasound is increased, the resolution of the ultrasound image (and its associated data) will be increased. For example, in some embodiments it may be advantageous to use an ultrasound probe capable of using micro-ultrasound or high resolution ultrasound (e.g., an ultrasound 29 MHz probe) to obtain ultrasound imaging data. The higher resolution may provide more detail that assists the operator in performing cognitive fusion.

Figure 13:
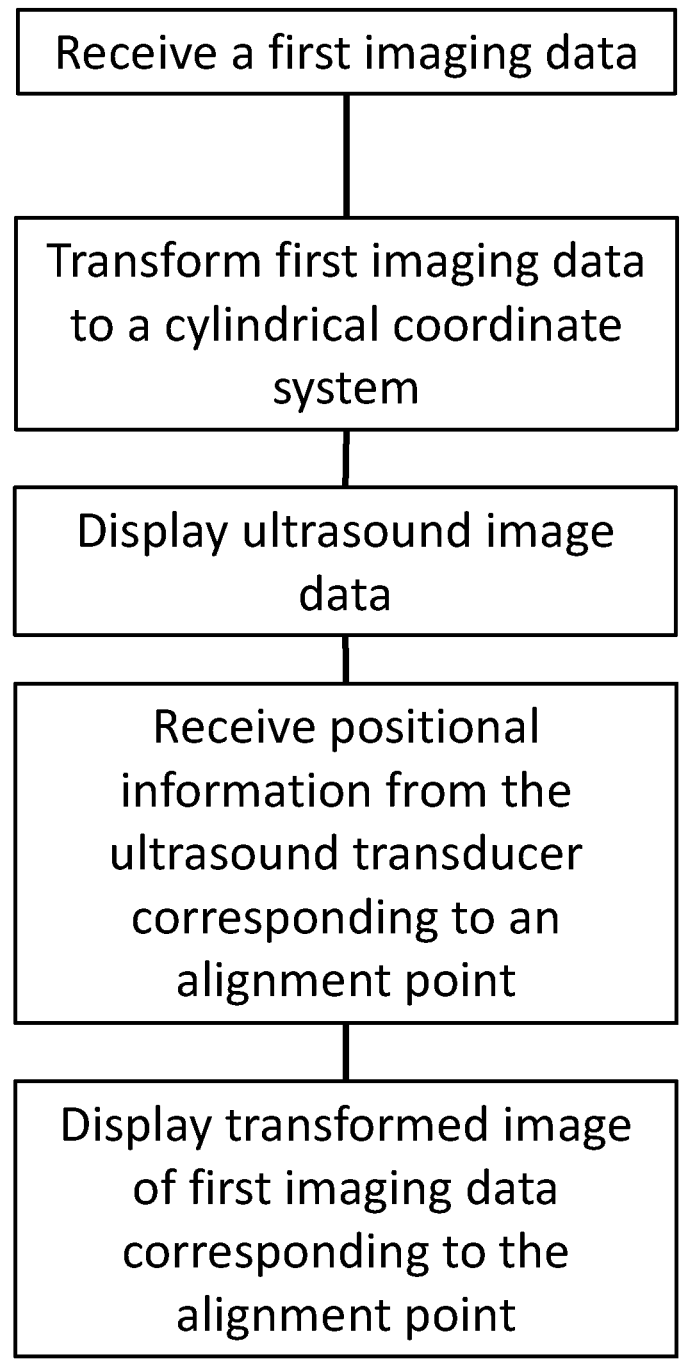
FIG. 13 (SHEET 26/27) depicts an embodiment method.

Referring now to FIG. 13 (SHEET 26/27), an example method for visually assisting an operator of an ultrasound system is provided. The method includes receiving a first imaging data of a first prostate using a first coordinate system. In this embodiment the first imaging data is previously captured MRI data. The first imaging data is marked with a landmark 800 for identifying the first prostate. In some examples the landmark 800 is sealed so that an approximate size of the prostate can be determined from the landmark 800. The first imaging data is then transformed from the first coordinate system to a cylindrical coordinate system. As was discussed, various algorithms for transforming data from a coordinate space to a cylindrical coordinate space are known (e.g., nearest neighbor, bi-linear interpolation, and/or bi-cubic). As ultrasound image data is being collected from a patient, a live ultrasound image of a second prostate as received from an ultrasound transducer is displayed. Furthermore, as the ultrasound image data is collected, positional information from the ultrasound transducer corresponding to an alignment point of the prostate is received. For example, the positional information can be obtained from roll sensors in the ultrasound transducer. The transformed image from the transformed first imaging data of the first prostate corresponding to the alignment point using the landmark 800 is then displayed in such a way so that the transformed image and the live ultrasound image are displayed simultaneously, for example on a display.

In another embodiment, a visual assistance interface is provided. The visual assistance interface may supplement or replace the displaying of the transformed image. The visual assistance interface may be a list of regions of interest or target landmarks and the corresponding roll angles (for guiding the movement of the ultrasound transducer by the operator) to show or target the region of interest or target. For example, a text box showing that a first region of interest is at −40 degrees (roll angle), and a second region of interest is at +30 degrees (roll angle). Another embodiment of the visual assistance interface may be an angle meter for showing the current roll angle (or positional information) of the ultrasound transducer. The visual assistance interface for showing the roll angle may be a text box showing the current roll angle (or positional information) or a graphical element such as an analog instrument gauge showing the roll angle (or positional information). In another embodiment, the visual assistance interface is shown along with the displayed transformed image. In another embodiment, the visual assistance interface is shown along with the displayed generated image.

As the ultrasound transducer 606 is moved, new positional information from the ultrasound transducer 606 is sent. Once this new positional information from the ultrasound transducer is received, the transformed image and the live ultrasound image corresponding to the new positional information of the ultrasound transducer are displayed simultaneously.

In another embodiment, the first imaging data is also marked with a region of interest in the prostate. During the transformation this region of interest is also transformed so that the transformed first image data also includes the region of interest information. As the ultrasound transducer 606 transmits new positional information, a determination is made whether the new positional information corresponds to the region of interest in the transformed first image data. If the region of interest is in the transformed image data corresponding to the new positional information, then a visual indicator of the region of interest is displayed on the transformed image.

In another embodiment, the ultrasound transducer provides positional information including roll, pitch, and yaw from the IMU. The roll, pitch and yaw information are used to track how the ultrasound probe is being moved in 3D space. For example, the pitch and yaw positional information tracks how the cylinder or "fan-shape" model of the ultrasound images (or image data) is being moved in 3D space. The roll, pitch, and yaw positional information allows for more accurate tracking and modelling of the movement of the ultrasound transducer. This may allow for more accurate tracking between the live ultrasound image data and first imaging data (e.g. the recorded ultrasound data or MRI scan). Or, this may allow for more accurate tracking between the live ultrasound image data and the 3D model anatomical region (e.g. 3D model prostate).

In another embodiment the first imaging data is recorded ultrasound imaging data of the prostate, and the first coordinate system is a cylindrical coordinate system.

It will be appreciated that the first prostate (as captured in previous image data) and the second prostate (as captured by live ultrasound) are the same prostate—that is, the prostate belongs to the same patient even though the imaging data of the first prostate and the second prostate may be separated by time. In some embodiments the time between when the first imaging data and the second imaging data may be within hours, days, or weeks. In other embodiments the separation of time is more significant (e.g., months, years). It will be appreciated that longer separations of time may be useful for long-term monitoring of the prostate. In contrast, shorter separations of time may be more useful for biopsies and/or diagnosis purposes.

In some embodiments the first imaging data is magnetic resonance imaging (MRI) data and the first coordinate system is a Cartesian coordinate system. Other imaging data formats and coordinate systems can be used without departing from the scope of this disclosure. For instance, in another embodiment the first imaging data is ultrasound data and the first coordinate system is a cylindrical coordinate system.

In some embodiments the landmark 800 is a line along a border between a rectal wall and the first prostate in a midline frame of a sagittal series of image frames of the first imaging data. The landmark 800 can also identify or provide information regarding the approximate size and orientation of the prostate.

In an embodiment the positional information is a roll angle of the ultrasound transducer. This roll angle information can be collected, for example, by a roll sensor incorporated in the ultrasound transducer.

In an embodiment the positional information is a roll angle of about 0 degrees and the alignment point is a mid-line of the second prostate. In another embodiment the positional information is a roll angle from about +80 degrees to about −80 degrees.

In an embodiment the ultrasound probe is a side-fire ultrasound probe.

In an embodiment the transformed image and the live ultrasound image are displayed side-by-side. In another embodiment the transformed image and the corresponding ultrasound image are displayed overlaid.

Figure 14:
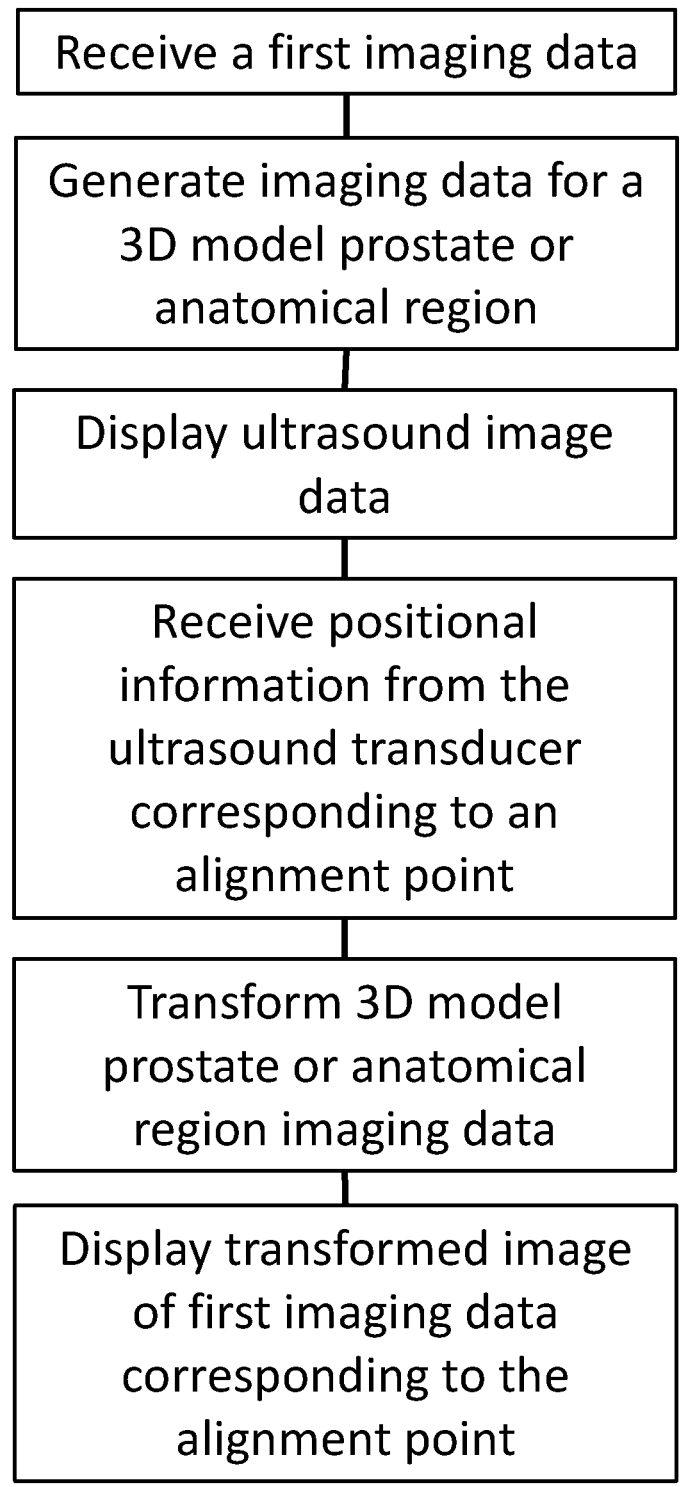
FIG. 14 (SHEET 27/27) depicts an alternate embodiment method.

Referring now to FIG. 14 (SHEET 27/27), in another embodiment a method for visually assisting an operator of an ultrasound system is provided. The method includes generating imaging data for a 3D model prostate that is in a cylindrical coordinate space. A live ultrasound image of a prostate as received from an ultrasound transducer is then displayed. Positional information from the ultrasound transducer corresponding to alignment points of the prostate is also received. Once the positional information corresponding to the alignment points is received the imaging data of the 3D model prostate is transformed. This transformation can include, but is not limited to, stretching, shrinking, and/or adjusting the 3D model of the prostate so that it approximately corresponds to the prostate. The generated image from the generated imaging data of the 3D model prostate corresponding to the positional information of the ultrasound transducer is then displayed. In this embodiment the generated image and the live ultrasound image are displayed simultaneously for visually assisting the operator of the ultrasound system;

In another embodiment a region of interest for the 3D model prostate is received. As the ultrasound transducer 606 transmits new positional information, a determination is made whether the new positional information corresponds to the region of interest in the transformed 3D image data. If the region of interest is in the transformed image data corresponding to the new positional information, then a visual indicator of the region of interest is displayed on the transformed image.

A region of interest for the 3D model prostate can be received in a variety of ways. This can include, but is not limited to, providing a graphical user interface for the selection of a region of interest of the 3D model prostate by the operator. In an embodiment, an input device is provided that allows an operator to input the region of interest.

It will be appreciated that the 3D model of the prostate can be subdivided into various zones and/or regions. The number of zones and/or regions can depend, for example, on the type of MRI reporting (e.g., PI-RADS, etc). For example. In some embodiments the 3D model of the prostate has 39 regions of interest.

In some embodiments the positional information is a roll angle of the ultrasound transducer.

In some embodiments the alignment points are the positional information of the ultrasound transducer corresponding to a left edge of the prostate, a mid-line of the prostate, and a right edge of the prostate.

In some embodiments the transforming is a scaling transformation of the image data.

The following clauses are offered as further description of the examples of the apparatus. Any one or more of the following clauses may be combinable with any another one or more of the following clauses and/or with any subsection or a portion or portions of any other clause and/or combination and permutation of clauses. Any one of the following clauses may stand on its own merit without having to be combined with any other clause or any portion of any other clause, etc. CLAUSE 1: A method for visually assisting an operator of an ultrasound system, comprising: receiving a first imaging data of a first anatomical region using a first coordinate system, the first imaging data marked with a landmark for identifying the first anatomical region; transforming the first imaging data of the first anatomical region from the first coordinate system to a cylindrical coordinate system; displaying a live ultrasound image of a second anatomical region as received from an ultrasound transducer; receiving positional information from the ultrasound transducer corresponding to an alignment point of the second anatomical region; and displaying a transformed image from the transformed first imaging data of the first anatomical region corresponding to the alignment point using the landmark. CLAUSE 2: A method of any of the clauses, or any portion of any clause, mentioned in this paragraph wherein the transformed image and the live ultrasound image are displayed simultaneously. CLAUSE 3: A method of any of the clauses, or any portion of any clause, mentioned in this paragraph further comprising the steps of receiving new positional information from the ultrasound transducer; and displaying both the transformed image and the live ultrasound image corresponding to the new positional information of the ultrasound transducer. CLAUSE 4: A method of any of the clauses, or any portion of any clause, mentioned in this paragraph further comprising the steps of: receiving the first imaging data, the first imaging data being marked with a region of interest in or on the first anatomical region; determining if the region of interest is visible in the transformed image corresponding to the positional information received; and once determining that the regions of interest is visible, then showing a visual indicator of the region of interest on the transformed image. CLAUSE 5: A method of any of the clauses, or any portion of any clause, mentioned in this paragraph wherein the first imaging data is recorded ultrasound imaging data of the first anatomical region, and the first coordinate system is a cylindrical coordinate system. CLAUSE 6: A method of any of the clauses, or any portion of any clause, mentioned in this paragraph further comprising wherein the first anatomical region and the second anatomical region are the same anatomical region. CLAUSE 7: A method of any of the clauses, or any portion of any clause, mentioned in this paragraph wherein the first imaging data is magnetic resonance imaging (MRI) data and the first coordinate system is a Cartesian coordinate system. CLAUSE 8: A method of any of the clauses, or any portion of any clause, mentioned in this paragraph wherein the landmark is a line along a border between a rectal wall and the first anatomical region in a midline frame of a sagittal series of image frames of the first imaging data. CLAUSE 9: A method of any of the clauses, or any portion of any clause, mentioned in this paragraph wherein the landmark identifies the approximate size and orientation of the anatomical region. CLAUSE 10: A method of any of the clauses, or any portion of any clause, mentioned in this paragraph wherein the positional information is a roll angle of the ultrasound transducer. CLAUSE 11: A method of any of the clauses, or any portion of any clause, mentioned in this paragraph wherein the positional information is a roll angle of about 0 degrees and the alignment point is a mid-line of the second anatomical region. CLAUSE 12: A method of any of the clauses, or any portion of any clause, mentioned in this paragraph wherein the positional information is a roll angle from about +80 degrees to about −80 degrees. CLAUSE 13: A method of any of the clauses, or any portion of any clause, mentioned in this paragraph wherein the ultrasound probe is a side-fire ultrasound probe. CLAUSE 14: A method of any of the clauses, or any portion of any clause, mentioned in this paragraph wherein the transformed image and the live ultrasound image are displayed side-by-side. CLAUSE 15: A method of any of the clauses, or any portion of any clause, mentioned in this paragraph wherein the transformed image and the corresponding ultrasound image are displayed overlaid. CLAUSE 16: A method of any of the clauses, or any portion of any clause, mentioned in this paragraph wherein the first anatomical region and the second anatomical region are the same anatomical region of a patient. CLAUSE 17: A method of any of the clauses, or any portion of any clause, mentioned in this paragraph wherein the anatomical region is a prostate. CLAUSE 18: A method of any of the clauses, or any portion of any clause, mentioned in this paragraph wherein the anatomical region is an organ, organ system, tissue, thyroid, rectum, or urinary tract. CLAUSE 19: A method of any of the clauses, or any portion of any clause, mentioned in this paragraph further comprising a method for visually assisting an operator of an ultrasound system, comprising: generating imaging data for a 3D model anatomical region, the imaging data in a cylindrical coordinate space; displaying a live ultrasound image of an anatomical region as received from an ultrasound transducer; receiving positional information from the ultrasound transducer corresponding to alignment points of the anatomical region; transforming the imaging data of the 3D model anatomical region based on the received positional information corresponding to the alignment points; and displaying a generated image from the generated imaging data of the 3D model anatomical region corresponding to the positional information of the ultrasound transducer; wherein the generated image and the live ultrasound image are displayed simultaneously for visually assisting the operator of the ultrasound system. CLAUSE 20: A method of any of the clauses, or any portion of any clause, mentioned in this paragraph further comprising receiving a region of interest for the 3D model anatomical region; determining if the region of interest is visible in the generated image corresponding to the positional information received; and once determining that the region of interest is visible, then showing a visual indicator of the region of interest on the generated image. CLAUSE 21: A method of any of the clauses, or any portion of any clause, mentioned in this paragraph further comprising providing a graphical user interface for the selection of a region of interest of the 3D model anatomical region by the operator. CLAUSE 22: A method of any of the clauses, or any portion of any clause, mentioned in this paragraph wherein the 3D model of the anatomical region has 39 regions of interest. CLAUSE 23: A method of any of the clauses, or any portion of any clause, mentioned in this paragraph wherein the positional information is a roll angle of the ultrasound transducer. CLAUSE 24: A method of any of the clauses, or any portion of any clause, mentioned in this paragraph wherein the alignment points are the positional information of the ultrasound transducer corresponding to a left edge of the anatomical region, a mid-line of the anatomical region, and a right edge of the anatomical region. CLAUSE 25: A method of any of the clauses, or any portion of any clause, mentioned in this paragraph wherein the transforming is a scaling transformation of the image data. CLAUSE 26: A method of any of the clauses, or any portion of any clause, mentioned in this paragraph wherein the positional information is a roll angle from about +80 degrees to about −80 degrees. CLAUSE 27: A method of any of the clauses, or any portion of any clause, mentioned in this paragraph wherein the ultrasound probe is a side-fire ultrasound probe. CLAUSE 28: A method of any of the clauses, or any portion of any clause, mentioned in this paragraph wherein the transformed image and the live ultrasound image are displayed side-by-side. CLAUSE 29: A method of any of the clauses, or any portion of any clause, mentioned in this paragraph wherein the transformed image and the corresponding ultrasound image are displayed overlaid. CLAUSE 30: A method of any of the clauses, or any portion of any clause, mentioned in this paragraph wherein the first anatomical region and the second anatomical region are the same anatomical region of a patient. CLAUSE 31: A method of any of the clauses, or any portion of any clause, mentioned in this paragraph wherein the anatomical region is a prostate. CLAUSE 32: A method of any of the clauses, or any portion of any clause, mentioned in this paragraph wherein the anatomical region is an organ, organ system, tissue, thyroid, rectum, or urinary tract. CLAUSE 33: A system for visually assisting an operator of an ultrasound system of any of the clauses, or any portion of any clause, mentioned in this paragraph comprising a data store for storing a first imaging data of a first anatomical region using a first coordinate system, the first imaging data marked with a landmark for identifying the first anatomical region; an ultrasound probe 606 for collecting: live ultrasound image data of a second anatomical region, and positional information from the ultrasound transducer, including positional information corresponding to an alignment point of the second anatomical region; a processing unit 602 for: receiving positional information from the ultrasound transducer corresponding to the alignment point of the second anatomical region, and transforming the first imaging data of the first anatomical region from the first coordinate system to a cylindrical coordinate system; and a display device 600 for displaying both the transformed image and the ultrasound image data corresponding to the positional information of the ultrasound transducer. CLAUSE 34: A system of any of the clauses, or any portion of any clause, mentioned in this paragraph further comprising an input device 600 for receiving a first imaging data of a first anatomical region using a first coordinate system. CLAUSE 35: A system of any of the clauses, or any portion of any clause, mentioned in this paragraph comprising a system for visually assisting an operator of an ultrasound system comprising: a data store for storing a 3D model anatomical region imaging data, the 3D model anatomical region imaging data in a cylindrical coordinate space; an ultrasound probe 606 for collecting: live ultrasound image data of a second anatomical region, and positional information from the ultrasound transducer, including positional information corresponding to an alignment point of the second anatomical region; a processing unit 602 for: receiving positional information from the ultrasound transducer corresponding to the alignment point of the second anatomical region, and transforming the 3D model anatomical region imaging data based on the received positional information corresponding to the alignment point of the second anatomical region; and a display device 600 for displaying both the transformed image and the ultrasound image data corresponding to the positional information of the ultrasound transducer. CLAUSE 36: A system of any of the clauses, or any portion of any clause, mentioned in this paragraph further comprising an input device 600 for receiving a region of interest for the 3D model anatomical region, CLAUSE 37. A method for visually assisting an operator of an ultrasound system, comprising, receiving a first imaging data of a first anatomical region using a first coordinate system, the first imaging data marked with a landmark for identifying the first anatomical region; transforming the first imaging data of the first anatomical region from the first coordinate system to a cylindrical coordinate system; displaying a live ultrasound image of a second anatomical region as received from an ultrasound transducer; receiving positional information from the ultrasound transducer corresponding to an alignment point of the second anatomical region; and displaying a visual assistance interface; wherein the visual assistance interface and the live ultrasound image are displayed simultaneously. CLAUSE 38: A method of any of the clauses, or any portion of any clause, mentioned in this paragraph, further comprising: displaying a transformed image from the transformed first imaging data of the first anatomical region corresponding to the alignment point using the landmark; wherein the transformed image and/or the visual assistance interface, and the live ultrasound image are displayed simultaneously. CLAUSE 39: A method for visually assisting an operator of an ultrasound system, comprising: generating imaging data for a 3D model anatomical region, the imaging data in a cylindrical coordinate space; displaying a live ultrasound image of an anatomical region as received from an ultrasound transducer; receiving positional information from the ultrasound transducer corresponding to alignment points of the anatomical region; transforming the imaging data of the 3D model anatomical region based on the received positional information corresponding to the alignment points; and displaying a visual assistance interface; wherein the visual assistance and the live ultrasound image are displayed simultaneously. CLAUSE 40. A method of any of the clauses, or any portion of any clause, mentioned in this paragraph, further comprising: displaying a generated image from the generated imaging data of the 3D model anatomical region corresponding to the positional information of the ultrasound transducer; wherein the generated image and/or the visual assistance interface, and the live ultrasound image are displayed simultaneously. CLAUSE 41: A system for visually assisting an operator of an ultrasound system comprising: a data store for storing a first imaging data of a first anatomical region using a first coordinate system, the first imaging data marked with a landmark for identifying the first anatomical region; an ultrasound probe 606 for collecting: live ultrasound image data of a second anatomical region, and positional information from the ultrasound transducer, including positional information corresponding to an alignment point of the second anatomical region; a processing unit 602 for: receiving positional information from the ultrasound transducer corresponding to the alignment point of the second anatomical region, and transforming the first imaging data of the first anatomical region from the first coordinate system to a cylindrical coordinate system; and a display device 600 for displaying both a visual assistance interface and the ultrasound image data corresponding to the positional information of the ultrasound transducer. CLAUSE 42: A system for visually assisting an operator of an ultrasound system comprising: a data store for storing a 3D model anatomical region imaging data, the 3D model anatomical region imaging data in a cylindrical coordinate space; an ultrasound probe 606 for collecting: live ultrasound image data of a second anatomical region, and positional information from the ultrasound transducer, including positional information corresponding to an alignment point of the second anatomical region; a processing unit 602 for: receiving positional information from the ultrasound transducer corresponding to the alignment point of the second anatomical region, and transforming the 3D model anatomical region imaging data based on the received positional information corresponding to the alignment point of the second anatomical region; and a display device 600 for displaying both a visual assistance interface and the ultrasound image data corresponding to the positional information of the ultrasound transducer. CLAUSE 43: A system of any of the clauses, or any portion of any clause, mentioned in this paragraph, wherein: the display device 600 for displaying a visual assistance interface and/or the transformed image, and the ultrasound image data corresponding to the positional information of the ultrasound transducer.

This written description uses examples to disclose the invention, including the best mode, and also to enable any person skilled in the art to make and use the invention. The patentable scope of the invention is defined by the claims, and may include other examples that occur to those skilled in the art. Such other examples are within the scope of the claims if they have structural elements that do not differ from the literal language of the claims, or if they include equivalent structural elements with insubstantial differences from the literal language of the claims.

It may be appreciated that the assemblies and modules described above may be connected with each other as required to perform desired functions and tasks within the scope of persons of skill in the art to make such combinations and permutations without having to describe each and every one in explicit terms. There is no particular assembly or component that may be superior to any of the equivalents available to the person skilled in the art. There is no particular mode of practicing the disclosed subject matter that is superior to others, so long as the functions may be performed. It is believed that all the crucial aspects of the disclosed subject matter have been provided in this document. It is understood that the scope of the present invention is limited to the scope provided by the independent claim(s), and it is also understood that the scope of the present invention is not limited to: (i) the dependent claims, (ii) the detailed description of the non-limiting embodiments, (iii) the summary, (iv) the abstract, and/or (v) the description provided outside of this document (that is, outside of the instant application as filed, as prosecuted, and/or as granted). It is understood, for this document, that the phrase "includes" is equivalent to the word "comprising." The foregoing has outlined the non-limiting embodiments (examples). The description is made for particular non-limiting embodiments (examples). It is understood that the non-limiting embodiments are merely illustrative as examples.

What is claimed is:

1. A method for visually assisting an operator of an ultrasound system, comprising:
   receiving a first imaging data of a first anatomical region using a first coordinate system, the first imaging data marked with a landmark for identifying the first anatomical region;
   transforming the first imaging data of the first anatomical region from the first coordinate system to a cylindrical coordinate system, wherein the first coordinate system is different from the cylindrical coordinate system;
   displaying a live ultrasound image of a second anatomical region as received from an ultrasound transducer;
   receiving positional information for the ultrasound transducer corresponding to an alignment line of the second anatomical region, the alignment line being a user selected line of the second anatomical region corresponding to the landmark in the first anatomical region, and the positional information being a roll angle of the ultrasound transducer corresponding to the alignment line; and
   wherein, the landmark and the positional information for the ultrasound transducer corresponding to the alignment line of the second anatomical region are for aligning the first imaging data to the live ultrasound image;
   displaying a transformed image from the transformed first imaging data of the first anatomical region corresponding to the alignment line, and the transformed image includes the landmark;
   wherein the transformed image and the live ultrasound image are displayed simultaneously;
   overlaying indicia on the transformed image indicating the roll angle of the ultrasound transducer, wherein the indicia changes in response to a change in the roll angle of the ultrasound transducer.

2. The method of claim 1, further comprising the steps of:
   receiving the first imaging data, the first imaging data being marked with a region of interest in or on the first anatomical region;
   determining if the region of interest is visible in the transformed image corresponding to the positional information received; and
   once determining that the regions of interest is visible, then showing a visual indicator of the region of interest on the transformed image.

3. The method of claim 2, wherein the positional information is a roll angle of a side-fire ultrasound transducer.

4. The method of claim 3, wherein the first anatomical region and the second anatomical region are the same anatomical region, and the anatomical region is a prostate.

5. The method of claim 4, wherein the landmark identifies the approximate size and orientation of the anatomical region, and, is a line along a border between a rectal wall and the first anatomical region in a midline frame of a sagittal series of image frames of the first imaging data.

6. The method of claim 5, wherein the first imaging data is magnetic resonance imaging (MRI) data and the first coordinate system is a Cartesian coordinate system.

7. The method of claim 5, wherein the first imaging data is recorded ultrasound imaging data of the first anatomical region.

8. The method of claim 1, wherein:
the first anatomical region is a pre-rendered 3D representative model anatomical region and the first coordinate system.

9. The method of claim 8, further comprising:
receiving second positional information for the ultrasound transducer corresponding to second alignment lines of the second anatomical region;
transforming the first imaging data of the 3D model anatomical region based on the received positional information corresponding to the alignment line and the second alignment lines.

10. The method of claim 9, further comprising:
displaying a generated image from the first imaging data of the 3D model anatomical region corresponding to the positional information of the ultrasound transducer.

11. The method of claim 10, further comprising:
receiving a region of interest for the 3D model anatomical region;
determining if the region of interest is visible in the generated image corresponding to the positional information received; and
once determining that the region of interest is visible, then showing a visual indicator of the region of interest on the generated image.

12. The method of claim 11, wherein the alignment lines and the second alignment lines are the positional information of the ultrasound transducer corresponding to a left edge of the anatomical region, a mid-line of the anatomical region, and a right edge of the anatomical region.

13. The method of claim 12, wherein the positional information is a roll angle of a side-fire ultrasound transducer.

14. The method of claim 13, wherein the first anatomical region and the second anatomical region are the same anatomical region, and the anatomical region is a prostate.

15. The method of claim 11, further comprising: providing a graphical user interface for the selection of a region of interest of the 3D model anatomical region by the operator.

16. A system for visually assisting an operator of an ultrasound system comprising:
a data store for storing a first imaging data of a first anatomical region using a first coordinate system, the first imaging data marked with a landmark for identifying the first anatomical region;
an ultrasound transducer for collecting:
live ultrasound image data of a second anatomical region, and
positional information for the ultrasound transducer, including positional information corresponding to an alignment line of the second anatomical region;
a processing unit for:
receiving positional information for the ultrasound transducer corresponding to the alignment line of the second anatomical region, the alignment line being a user selected line of the second anatomical region corresponding to the landmark in the first anatomical region, and the positional information being a roll angle of the ultrasound transducer corresponding to the alignment line, wherein, the landmark and the positional information for the ultrasound transducer corresponding to the alignment line of the second anatomical region are for aligning the first imaging data to the live ultrasound image, and
transforming the first imaging data of the first anatomical region from the first coordinate system to a cylindrical coordinate system, wherein the first coordinate system is different than the cylindrical coordinate system; and
a display device for:
displaying the live ultrasound image of the second anatomical region;
displaying a transformed image from the transformed first imaging data of the first anatomical region corresponding to the alignment line that includes the landmark, wherein the transformed image and the live ultrasound image are displayed simultaneously; and
overlaying indicia on the transformed image indicating the roll angle of the ultrasound transducer, wherein the indicia changes in response to a change in the roll angle of the ultrasound transducer.

17. The system of claim 16, wherein the processing unit is further configured to:
receive the first imaging data, the first imaging data being marked with a region of interest in or on the first anatomical region;
determine if the region of interest is visible in the transformed image corresponding to the positional information received; and
once determined that the region of interest is visible, then showing on the display device a visual indicator of the region of interest on the transformed image.

18. The system of claim 17, wherein the positional information is a roll angle of a side-fire ultrasound transducer.

19. The system of claim 18, wherein the first anatomical region and the second anatomical region are the same anatomical region, and the anatomical region is a prostate.

20. The system of claim 19, wherein the landmark identifies the approximate size and orientation of the anatomical region, and, is a line along a border between a rectal wall and the first anatomical region in a midline frame of a sagittal series of image frames of the first imaging data.

21. The system of claim 20, wherein the first imaging data is magnetic resonance imaging (MRI) data and the first coordinate system is a Cartesian coordinate system.

22. The system of claim 20, wherein the first imaging data is recorded ultrasound imaging data of the first anatomical region.

23. The system of claim 16, wherein:
the first anatomical region is a pre-rendered 3D representative model anatomical region.

24. The system of claim 23, wherein the processing unit is further configured to:
receive second positional information for the ultrasound transducer corresponding to second alignment lines of the second anatomical region;
transform the first imaging data of the 3D model anatomical region based on the received positional information corresponding to the alignment line and the second alignment lines.

25. The system of claim 24, wherein the processing unit is further configured to:

display on the display device a generated image from the first imaging data of the 3D model anatomical region corresponding to the positional information of the ultrasound transducer.

26. The system of claim 25, further comprising:
an input device for receiving a region of interest for the 3D model anatomical region; and the processor is further configured to:
determine if the region of interest is visible in the generated image corresponding to the positional information received; and
once determined that the region of interest is visible, then showing a visual indicator of the region of interest on the generated image on the display device.

27. The system of claim 26, wherein the alignment lines and the second alignment lines are the positional information of the ultrasound transducer corresponding to a left edge of the anatomical region, a mid-line of the anatomical region, and a right edge of the anatomical region.

28. The system of claim 27, wherein the positional information is a roll angle of a side-fire ultrasound transducer.

29. The system of claim 28, wherein the first anatomical region and the second anatomical region are the same anatomical region, and the anatomical region is a prostate.

30. The system of claim 26, wherein the processing unit is further configured to: display on the display device a graphical user interface for the selection of a region of interest of the 3D model anatomical region by the operator.

31. The method of claim 1, wherein the live ultrasound image represents an image plane of the second anatomical region, and the indicia represents an intersection of the image plane and the first anatomical region as characterized in the transformed image.

32. The system of claim 16, wherein the live ultrasound image represents an image plane of the second anatomical region, and the indicia represents an intersection of the image plane and the first anatomical region as characterized in the transformed image.

33. The method of claim 1, wherein the transformed image comprises a first transformed image and a second transformed image, such that the first transformed image, the second transformed image and the live ultrasound image are displayed simultaneously, and the indicia is overlaid on the first transformed image, and wherein the second transformed image represents a portion of an image plane that is transverse to the indicia, such that the second transformed image changes in response to the change in the roll angle of the ultrasound transducer.

* * * * *